(12) United States Patent
LeBoeuf et al.

(10) Patent No.: US 8,425,858 B2
(45) Date of Patent: Apr. 23, 2013

(54) DETECTION APPARATUS AND ASSOCIATED METHOD

(75) Inventors: Steven Francis LeBoeuf, Schenectady, NY (US); Peter Micah Sandvik, Clifton Park, NY (US); Radislav Alexandrovich Potyrailo, Niskayuna, NY (US)

(73) Assignee: Morpho Detection, Inc., Newark, CA (US)

( * ) Notice: Subject to any disclaimer, the term of this patent is extended or adjusted under 35 U.S.C. 154(b) by 898 days.

(21) Appl. No.: 11/480,068

(22) Filed: Jun. 30, 2006

(65) Prior Publication Data

US 2007/0086915 A1 Apr. 19, 2007

Related U.S. Application Data

(60) Provisional application No. 60/727,914, filed on Oct. 14, 2005.

(51) Int. Cl.
*G01N 31/22* (2006.01)

(52) U.S. Cl.
USPC ............ 422/400; 117/952; 257/103; 438/22; 438/24; 438/29

(58) Field of Classification Search ............... 438/689; 204/415; 117/95–98; 73/31.06; 428/402; 422/88
See application file for complete search history.

(56) References Cited

U.S. PATENT DOCUMENTS

| | | | |
|---|---|---|---|
| 5,578,839 A | 11/1996 | Nakamura et al. | |
| 5,637,531 A | 6/1997 | Porowski et al. | |
| 5,658,444 A * | 8/1997 | Black et al. | 204/403.09 |
| 5,770,887 A | 6/1998 | Tadatomo et al. | |
| 5,810,925 A | 9/1998 | Tadatomo et al. | |
| 6,015,979 A | 1/2000 | Sugiura et al. | |
| 6,140,669 A | 10/2000 | Lozykowski et al. | |
| 6,181,721 B1 | 1/2001 | Geels et al. | |
| 6,225,650 B1 | 5/2001 | Tadatomo et al. | |

(Continued)

FOREIGN PATENT DOCUMENTS

| WO | WO 01/24285 | 4/2001 |
|---|---|---|
| WO | WO 01/37351 | 5/2001 |

OTHER PUBLICATIONS

Dwilinski et al., Excitation photo-luminescence of GaN bulk crystals grown by the AMMONO method, 1997, Elsevier Science S.A., Materials Science and Engineering B50, p. 46-49.*

(Continued)

*Primary Examiner* — In Suk Bullock
*Assistant Examiner* — Robert Eom
(74) *Attorney, Agent, or Firm* — Armstrong Teasdale LLP

(57) ABSTRACT

An apparatus includes an article and a detector. The article includes a substrate, a faceted structure disposed on the substrate, and a sensor layer disposed on the faceted structure. The faceted structure is disposed on the substrate first surface and itself has a surface. The faceted structure surface has peripheral edge defining a diameter of the faceted structure surface. The sensor layer is disposed on the faceted structure surface. The sensor layer can react or can interact with a target species when the target species is sufficiently proximate to the sensor layer. The sensor layer responds to the reaction or to the interaction in a detectable manner. The detector detects a response to the reaction, or to the interaction, of the target species with the sensor layer.

35 Claims, 11 Drawing Sheets

U.S. PATENT DOCUMENTS

| | | | |
|---|---|---|---|
| 6,255,669 B1 | 7/2001 | Birkhahn et al. | |
| 6,281,526 B1 | 8/2001 | Nitta et al. | |
| 6,294,440 B1 | 9/2001 | Tsuda et al. | |
| 6,325,850 B1* | 12/2001 | Beaumont et al. | 117/95 |
| 6,413,627 B1 | 7/2002 | Motoki et al. | |
| 6,468,347 B1* | 10/2002 | Motoki et al. | 117/89 |
| 6,492,182 B1 | 12/2002 | Bright et al. | |
| 6,596,079 B1 | 7/2003 | Vaudo et al. | |
| 6,680,206 B1 | 1/2004 | McDevitt et al. | |
| 6,686,691 B1 | 2/2004 | Mueller et al. | |
| 6,700,179 B1 | 3/2004 | Ouchi et al. | |
| 2002/0178789 A1* | 12/2002 | Sunshine et al. | 73/31.06 |
| 2004/0124434 A1 | 7/2004 | D'Evelyn et al. | |
| 2004/0180203 A1* | 9/2004 | Yadav et al. | 428/402 |
| 2004/0261692 A1* | 12/2004 | Dwilinski et al. | 117/84 |
| 2005/0230356 A1* | 10/2005 | Empedocles et al. | 217/2 |

OTHER PUBLICATIONS

Yoon et al., Electroreflectance and photoluminescence study of InN, 2005, IOP Publishing Ltd., Semiconductor Science and Technology 20 (2005), p. 1068-1071.*

Yang et al., Optical properties of titanium oxynitride nanocrystals synthesized via a thermal liquid-solid metathesis reaction, 2004, Elsevier B.V., Chemical Physics Letters 383 (2004), p. 502-506.*

Jeong et al., Photoluminescence properties of SnO2 thin films grown by thermal CVD, 2003, Elsevier Ltd., Solid State Communications 127 (2003), p. 595-597.*

Ce Hurwitz, "High Power and Efficiency in CdS Electron Beam Pumped Lasers", Applied Physics Letters, vol. 9, No. 12, pp. 420-423, Dec. 15, 1966.

V. Daneu et al., "Electron-Pumped High-Efficiency Semiconductor Laser", Applied Physics Letters, vol. 49, No. 10, pp, 546-548, Sep. 8, 1986.

JF Asmus et al., "Pulse Broadening in a MHD Copper Vapor Laser", Applied Physics Letters, vol. 13, No. 11, pp. 384-385, Dec. 1, 1968.

JL Brewster, "Stimulated Emission From CdS at Ultra-High Current Density Electron Beam Pumping", Applied Physics Letters, vol. 13, No. 11, pp. 385-387, Dec. 1, 1968.

H. Klausing et al., "Electron Beam Pumping in Nitride Vertical Cavities With GaN/$A_{10.25}GA_{0.75}$N Bragg Reflectors", Laboratorium für Informationstechnologie, Universität Hannover, 30167 Hannover, Germany, 6 pages, Abstract.

S. Bidnyk et al., "Room Temperature Laser Action in Laterally Overgrown GaN Pyramids on (111) Silicon", Center for Laser and Photonics Research and Department of Physics, Oklahoma State University, Stillwater, Oklahoma 74078,6 pages, Cite this article as: MRS Internet J. Nitride Semicond. Res. 4S1, G6.48, 1999.

HX Jiang et al., "Optical Resonance Modes in GaN Pyramid Microcavities", Applied Physics Letters, vol. 75, No. 6, pp. 763-765, Aug. 9, 1999.

F. Bertram et al., American Institute of Physics, Applied Physics Letters, "Strain Relaxation and Strong Impurity Incorporation in Epitaxial Laterally Overgrown GaN: Direct Imaging of Different Growth Domains By Cathodoluminescence Microscopy and Micro-Raman Spectroscopy", vol. 74, No. 3, pp. 359-361, Jun. 26, 2000.

P. Fini et al., American Institute of Physics, Applied Physics Letters, "In Situ, Real-Time Measurement of Wing Tilt During Lateral Epitaxial Overgrowth of GaN", vol. 76, No. 26, pp. 3893-3895, Jun. 26, 2000.

P. Fini et al., Journal of Crystal Growth, Determination of Tilt in the Lateral Epitaxial Overgrowth of GaN Using X-Ray Diffraction, vol. 209, pp. 581-590, 2000.

Yoshiaki Honda et al., Japan Journal of Applied Physics, "Crystal Orientation Fluctuation of Epitaxial-Lateral-Overgrown GaN with W Mask and $SiO_2$ Mask Observed by Transmission Electron Diffraction and X-Ray Rocking Curves", vol. 38, Part 2, No. 11B, pp. L1299-L1302, Nov. 15, 1999.

K. Horibuchi et al., Threading Disclocations in SAG-GaN, Phys. Stat. Sol., "Behavior of Treading Disclocations in SAG-GaN Grown by MOVPE", 180, pp. 171-175, 2000.

Ig-Hyeon Kim et al., American Institute of Physics, Applied Physics Letters, "Crystal Tilting in GaN Grown By Pendoepitaxy Method on Sapphire Substrate", vol. 75, No. 26, pp. 4109-4111, Dec. 27, 1999.

TS Kuan et al., Department of Physics, University at Albany, State University of New York, Albany, NY 12222, "Dislocation Mechanisms in the GaN Lateral Overgrowth by Hydride Vapor Phase Epitaxy", F99W2.6, pp. 1-6.

H. Marchand et al., American Institute of Physics, Applied Physics Letters, "Microstructure of GaN Latgerally Overgrown by Metalorganic Chemical Vapor Deposition", vol. 73, No. 6, pp. 747-749, Aug. 10, 1998.

Akira Sakai et al., American Institute of Physics, Applied Physics Letters, "Transmission Electron Microscopy of Defects in GaN Films Formed by Epitaxial Lateral Overgrowth", vol. 73, No. 4, pp. 481-483, Jul. 27, 1998.

YH Song et al., Phys. Stat. Sol., Lateral Epitaxial Overgrowth of GaN and Its Crystallographic Tilt Depending on the Growth Condition, 180, pp. 247-250, 2000.

S. Tomiya et al., American Institute of Physics, Applied Physics Letters, "Dependence of Crystallographic Tilt and Defect Distribution on Mask Material in Epitaxial Lateral Overgrown GaN Layers", vol. 77, No. 5, pp. 636-638, Jul. 31, 2000.

Chris G. Van de Walle, The American Physical Society, Rapid Communications, Physical Review B, "Interactions of Hydrogen With Native Defects in GaN", vol. 56, No. 16, pp. R10 020-R10 023, Oct. 15, 1997.

Marcie G. Weinstein et al., American Institute of Physics, Applied Physics Letters, "Hydrogen-Decorated Lattice Defects in Proton Implanted GaN", vol. 72, No. 14, pp. 1703-1705, Apr. 6, 1998.

R. P. Vaudo et al., Phys. Stat. Sol. (a) "GaN Boule Growth: A Pathway to GaN Wafers With Improved Material Quality", vol. 194, No. 2, pp. 494-497, 2000.

A. Yasan et al., American Institute of Physics, Applied Physics Letters, "Comparison of Ultraviolet Light-Emitting Diodes With Peak Emission at 340 nm Grown on GaN Substrate and Sapphire", vol. 81, No. 12, pp. 2151-2153, Sep. 16, 2002.

I. Grzegory et al., Acta Physica Polonica A, High Pressure Research Center, Polish Academy of Sciences, Unipress, Sokolowska 29/37, 01-142 Warsaw, Poland, "Blue Laser on High N2 Pressure-Grown Bulk GaN", vol. 100, pp. 229-232, 2001.

P. Prystawko et al., Phys. Stat. Sol. (a) "Blue-Laser Structures Grown on Bulk GaN Crystals", vol. 192, No. 2, pp. 320-324, 2002.

M. Kamp et al., "GaN Homoepitaxy for Device Applications", 12 pages, Cite this article as: MRS Internet J. Nitride Semicond. Res. 4S1, G10.2, High Pressure Research Center, Warsaw, Poland, 1999.

S. Porowski et al., Acta Physica Polonica A, High Pressure Research Center, Polish Academy of Sciences, Sokolowska 29/37, 01-142 Warsaw, Poland, "High Resistivity GaN Single Crystalline Substrates", vol. 92, No. 5, pp. 958-962, 1997.

J. I. Pankove et al., American Institute of Physics, Applied Physics Letters, "Molecular Doping of Gallium Nitride", vol. 74, No. 3, pp. 416-418, Jan. 18, 1999.

Arthur Pelzmann et al., Elsevier Science Bl.V., Journal of Crystal Growth, "Blue Light-Emitting Diodes on GaN Substrates, Growth and Characterization", vol. 189/190, pp. 167-171, 1998.

S. Porowski, "High Pressure Crystallization of III-V Nitrides", Acta Physica Polonica A, vol. 87, No. 2, pp. 295-302, 1995. Internet Journal Nitride Semiconductor Research 4S1, Article G1.3, 1999.

Co-pending U.S. Appl. No. 09/683,659, filed Jan. 31, 2002.
Co-pending U.S. Appl. No. 09/683,658, filed Jan. 31, 2002.
Co-pending U.S. Appl. No. 10/693,126, filed Oct. 24, 2003.
Co-pending U.S. Appl. No. 10/329,981, filed Dec. 27, 2002.
Co-pending U.S. Appl. No. 10/686,136, filed Oct. 15, 2003.

* cited by examiner

DETECTION APPARATUS AND ASSOCIATED METHOD

CROSS REFERENCE TO RELATED APPLICATIONS

This application claims the benefit of, and priority to, U.S. Provisional Application Ser. No. 60/727,914, filed 14 Oct. 2005, which is hereby incorporated by reference in its entirety.

BACKGROUND

1. Technical Field

The invention includes embodiments that relate to a crystalline composition. The invention includes embodiments that relate to an array of faceted structures. The invention includes embodiments that relate to a sensor device or sensor apparatus. The invention includes embodiments that relate to a method of making and/or using the crystalline composition, the faceted structure array, and/or the sensor device or sensor apparatus.

2. Discussion of Related Art

In applications ranging from metabolic diagnostics to detection of pathogenic organisms, biomolecules may be detected through either signal amplification or by antibody recognition. Signaling may be accomplished by attaching luminescent labels to probes. These conventional tests may be problematic.

Some sensor systems may combine the use of light-based sensors with the use of biomolecular probes. These systems may involve complex optics to route light to a zone where the probes can interact with the analyte. The cost and complexity renders such systems impractical for routine diagnostics or biohazard monitoring.

It may be desirable to have an apparatus that has different properties than those currently available. It may be desirable to have a method that differs from those currently available.

BRIEF DESCRIPTION

In one embodiment according to the invention, an apparatus includes an article and a detector. The article includes a substrate, a faceted structure disposed on the substrate, and a sensor layer disposed on the faceted structure. The faceted structure is disposed on the substrate first surface and itself has a surface. The faceted structure surface has peripheral edge defining a diameter of the faceted structure surface. The sensor layer is disposed on the faceted structure surface. The sensor layer can react or can interact with a target species when the target species is sufficiently proximate to the sensor layer. The sensor layer responds to the reaction or to the interaction in a detectable manner. The detector detects a response to the reaction, or to the interaction, of the target species with the sensor layer.

In one embodiment, an apparatus includes: means for forming an emission of radiation; means for modulating the emission in the presence of a target species, or means for changing emission in the presence of the target species; and means for detecting the changing or the modulating of the emission of radiation.

In one embodiment, a method includes directing a first radiation to a faceted structure capable of responding to the first radiation by emitting a second radiation, or by emitting the second radiation and scattering the first radiation. The second radiation is modulated in the presence of a first target species; the first radiation is scattered in the presence of the first target species, or of a second target species if present; or, both the first radiation is scattered and the second radiation is modulated in the presence of at least the first target species. The modulation of the second radiation is detected and information associated with the first target species is obtained. The information includes the presence, the quantity, or the identity of the first target species.

BRIEF DESCRIPTION OF DRAWING FIGURES

DETAILED DESCRIPTION

Figure 1:
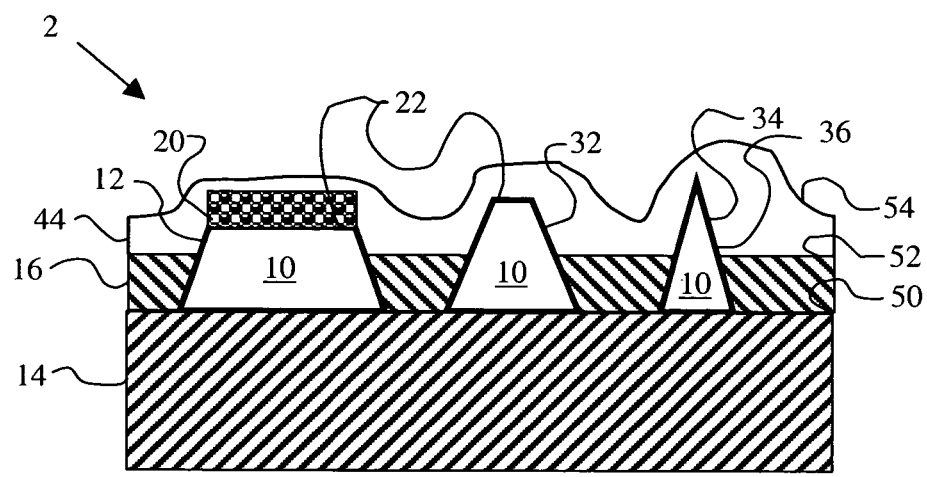
FIG. 1 is a representation of an exemplary crystalline composition or faceted structure array according to an embodiment of the invention.

The invention includes embodiments that relate to a crystalline composition. The invention includes embodiments that relate to an array of faceted structures. The invention includes embodiments that relate to a sensor device or sensor apparatus that includes the crystalline composition or faceted structure. The invention includes embodiments that relate to a method of making and/or using the crystalline composition, the faceted structure array, or the sensor device or sensor apparatus.

Approximating language, as used herein throughout the specification and claims, may be applied to modify any quantitative representation that could permissibly vary without resulting in a change in the basic function to which it is related. Accordingly, a value modified by a term or terms, such as "about", are not to be limited to the precise value specified. In some instances, the approximating language may correspond to the precision of an instrument for measuring the value.

A crystal is a body formed by the solidification of a chemical element, a compound, or a mixture, has a regularly repeating internal arrangement of atoms, and is bound by external plane faces (facets). A crystalline composition is a material that has one or more features associated with a crystal. The external plane faces or facets may be formed naturally upon growing the crystal or may be cleavage surfaces formed by cleaving as-grown crystals. Unless specified otherwise, reference to a facet is to a naturally grown facet and not to a cleavage surface. In the naturally grown facet, the orientation of the facet surface aligns with the crystal lattice of the medium material. The grown facet may differ from the cleavage surface in that naturally formed crystal facets tend to be relatively smooth; with a low surface roughness (for example, of less than about 50 nanometers RMS). Cleavage surfaces may be characterized by structural, electrical, topological, and/or morphological differences with a grown facet that are artifacts of the cleaving process. Such artifacts may include one or more of steps, cracks, and chips. As a result, the facet may reflect and/or absorb radiation differently relative to a cleavage surface. For example, a facet may be a more efficient reflector of electromagnetic radiation than a cleavage surface. Cathodoluminescence is an optical and electrical phenomenon where a beam of electrons generated by an electron gun (e.g. cathode ray tube) impacts on a luminescent material causing it to emit light. Other forms of luminescence differ in that they derive the excitation energy from another source. Because differing internal structures in a material may emit light differently, if at all, crystallographic differences, such as defects, may be identified by cathodoluminescence spectroscopy.

Polar refers to a surface with an electrical field normal to a surface plane of the surface; and non-Polar refers to a surface with little or no electrical field normal to the surface plane. Different faces of gallium-containing nitride, the Nitrogen face and the Metal face, have different surface charges and properties relative to each other. The surface of the Metal face has negative charge; and, the surface of the Nitrogen face has a positive charge. The Metal face is Lewis acidic and can interact with Lewis bases, and vice versa. In a gallium-only gallium nitride material, the metal face is exposed gallium molecules. In an aluminum gallium nitride material, the metal face can be gallium, aluminum, or both gallium and aluminum. This extends to other semiconductor compositions, such as InGaN and AlInGaN.

For purposes of this disclosure, reference is made to the base of the faceted structure, which has a base surface; the exposed surface is opposite the base surface; and side wall have side surfaces that extend at least partially from the base surface to the exposed surface and form some planar angle with the plane of the substrate surface. The base surface may contact the substrate surface, or an intervening layer on the substrate surface.

The side surfaces may be the same as each other or different from each other from embodiment to embodiment, for faceted structure to faceted structure in an array, or for side surface to side surface on a single faceted structure. Unless indicated by language or context, side surfaces of each faceted structure are about the same as each other on each faceted structure, and from one faceted structure to another in an array, with the exception that in an array that has differing surface area of the exposed surface across an array with the same base surface areas, the surface area of the side surfaces will differ. The side surfaces may be exactly perpendicular to the substrate plane, in one embodiment, and are referred to as platelets. A portion of one or more side surfaces may contact an inner surface that defines the aperture in the template layer that determines the diameter of the faceted structure.

In one embodiment, the exposed surface is the polar surface and the side surface is the relatively non-polar surface. This can be achieved, for example, by growing on a substrate that is c-plane GaN. While many of the examples herein, and discussion throughout, refers to the exposed surface being the surface on which the sensor layer is disposed, other embodiments may have the polarity reversed. For example, in one embodiment, the side surface is the polar surface and the exposed surface is the relatively non-polar surface. This can be achieved, for example, by growing on a substrate that is a-plane GaN. Further, the planar angle of the side surfaces, particularly the portion that extends beyond the template layer, can be controlled, and such control allows for tailoring of the side surface properties. In one embodiment, the side surfaces have more properties associated with a metal face. In one embodiment, the side surfaces have more properties associated with a nitrogen face. In one embodiment, the side surfaces have more properties associated with both metal and nitrogen faces, which may be achieved by the step-wise function of an angled plane through a crystal lattice structure. As the lattice is based on the composition, the atomic make-up at the surface differs as the planar angle differs. Controlling the planar angle accords control over the surface composition, and thus the surface properties.

The difference in the composition of the surfaces leads to differences in surface properties. As there is more than one surface adjacent to each other, this can lead to adjacent surfaces having differing properties being functionalized differently by surface treatments, such as spin coating and washing.

With reference to FIG. 1, a device 2 includes an array of detector functional components. The detector functional components are formed from a crystalline composition 10. The crystalline composition is formed as a faceted structure 12. The faceted structure is disposed on a substrate 14 within a template layer 16. The template layer may be removed subsequently in some embodiments. A sensor layer is supported by an exposed surface 22 of the crystalline composition. The faceted structure 12 is one of three illustrated faceted structures 12, 32, 34 formed from the crystalline composition and has the largest exposed surface area of the three faceted structures illustrated in the array. Each illustrated faceted structures 12, 32, 34 has a plurality of sidewalls 36. Apertures (no reference number) defined by the template layer differ in diameter from one to another. Reference number 32 indicates another of the faceted structures having relatively less exposed surface area and relatively more sidewall surface area. Yet another faceted structure has no apparent exposed surface area, larger amount of sidewall surface, and is indicated by the reference number 34. a sensor layer is shown only on one of the faceted structures for reasons of clarity of illustration, however other sensor layers may be supported on any or all of the other surfaces of the faceted structures illustrated. The three illustrated faceted structures 12, 32, 34 together define an array or a portion of the array, and the planar angle of the sidewalls of each differs. An optional exclusion layer 44 is shown disposed over the array. Each of the substrate, the template layer, and the exclusion layer has an outward facing surface 50, 52, 54.

In one embodiment, the crystalline composition includes a semiconductor material, and may be a direct wide bandgap semiconductor. Direct bandgap semiconductors may be efficient producers of photons relative to indirect bandgap materials. Suitable direct bandgap semiconductors include the group III-V semiconductors, which may include one or more elements from groups IIIB (e.g., boron, aluminum, gallium, indium) and VB (e.g., phosphorous, arsenic, nitrogen, antimony) of the Periodic Table. Gallium arsenide is a suitable group III-V semiconductor.

In one embodiment, the crystalline composition may include a nitride, an arsenide, a phosphide, a telluride, an antimide, or combinations of two or more of these. In one embodiment, the semiconductor may include a nitride having the formula $Al_xIn_yGa_{(1-x-y)}N$; where the sum x+y may be less than or equal to 1. This material, which may be currently in commercial use in products such as light emitting diodes (LEDs) and high electron mobility transistors (HEMTs), may be useful because the wavelengths of radiation emitted by the material may be controlled over a wide range (from ultraviolet to infrared) by controlling the compositional component amounts and faceted structure geometry.

In one embodiment, the crystalline composition includes a metal nitride. A suitable metal may include one or more of aluminum, boron, indium, or gallium. Other suitable metals may include the Group III elements—as listed in column 13 of the periodic table and sometimes referred to Group IIIA. Suitable metals include those with a +3 valence. In one embodiment, the metal nitride is aluminum nitride. In one embodiment, the metal nitride is gallium-containing nitride. In one embodiment, the metal nitride is indium gallium-containing nitride.

Although semiconductor materials may be suited for use as the crystalline composition, other materials may be suitable. Suitable other materials may include scintillator materials, such as rare-earth-doped yttrium aluminum garnet (YAG) and rare-earth-doped yttrium aluminum perovskite (YAP), may be an example. Other examples of scintillator materials and other materials suitable for the crystalline composition include lithium gallate, aluminum nitride (AlN), boron nitride (BN), diamond, barium fluoride ($BaF_2$), cadmium tungstate ($CdWO_4$), and bismuth germanium oxide (BGO). Further examples include phosphors, such as copper-doped zinc sulfide (ZnS:Cu), cerium-doped yttrium silicate, and phosphor compositions comprising rare earth elements such as lanthanum.

The crystalline composition as the faceted structure has an exposed surface, and the exposed surface has peripheral edge defining a diameter of the exposed surface. The diameter may be less than about 10 micrometer on average. The exposed surface may be a grain boundary or a facet. In one embodiment, the exposed surface is a grain boundary and is neither cut nor etched.

The crystalline composition may have an exposed surface with a polar orientation. The exposed surface may be a natural facet, a cleavage plane or an etched plane. In one embodiment, the orientation of the exposed surface is c-plane and in another the orientation is a-plane. The orientation and polarity of the exposed surface can be controlled. According to one aspect, the choice of substrate can control the properties of the exposed surface. Selecting a-plane gallium-containing nitride as the substrate surface accessible through apertures in the template layer will cause the exposed surface to be a-plane in the gallium-containing nitride faceted structures. Selecting c-plane gallium-containing nitride as the substrate surface accessible through apertures in the template layer will cause the exposed surface to be c-plane in the gallium-containing nitride faceted structures.

The crystalline composition exposed surface may have both a polar surface area, and a non-polar surface area adjacent to the polar surface area. The ratio of polar surface area to non-polar surface area is in a range of less than 10. In one embodiment, the ratio is in a range of from about 100 to about 25, from about 25 to about 10, from about 10 to about 5, from about 5 to about 2, from about 2 to about 1, or less than about 1. In one embodiment, the ratio is in a range of from about 1 to about 0.75, from about 0.75 to about 0.5, from about 0.5 to about 0.25, from about to about 0.1, or less than about 0.1. That is, there may be more polar surface area than non-polar surface area of the exposed surface.

The ratio of polar surface area to non-polar surface area is controllable via one or more techniques, which may be used in combination. One way of controlling the ratio is to control the aperture diameter in the template layer. Another way is to control the time of the crystalline composition growth, with completion of the crystal growth resulting no remaining exposed surface. Accordingly, for that way the deposition rate should be known and the growth process stopped prior to the exposed surface area going to zero.

In one embodiment, the polar orientation of the exposed surface may be the nitrogen face. In one embodiment, the polar orientation of the exposed surface may be the metal face. The polar orientation of the exposed surface may respond electrically to reaction or interaction with an acid relatively stronger than with a base. However, in another embodiment the polar orientation of the exposed surface responds electrically to reaction or interaction with a base relatively stronger than with an acid.

In one embodiment, the polarity or non-polarity of one or more faces may be inverted. For example, a positive polar exposed surface may be contacted with a molecular species that has a negative moiety and a non-polar tail. The negatively charged group reacts with the polar surface to form a covalent bond with a non-polar tail oriented away from the exposed surface. Thus, the observed polarity may be reduced or removed. Alternatively, a positive polar exposed surface may be contacted with a molecular species that has a negative moiety at first and second ends. One end may react with the positive polar surface, and the apparent polarity would be negative or inverted from the original positive charge. Selective additions of layers may be made that react, interact, or avoid based on the affinity of functional groups with particular surfaces of the faceted structure.

The exposed surface may be one of a plurality of exposed surfaces defined by the peripheral edge, and at least two of the plurality of exposed surfaces produce a differing electrical or optical response to the reaction or interaction of the target species, or to interaction with energy of a determined character. The polar orientation of the exposed surface responds electrically to reaction or interaction with one or more gas molecules in a measurable manner. The exposed surface may respond to the application of thermal energy by changing the electrical, or optical properties.

During use, the crystalline composition may respond to interaction with photons by generating an emission. In one embodiment, the emission is a stimulated emission. The crystalline composition response to incident energy may be strong in the spectral range of greater than about 150 nanometers, or less than about 2900 nanometers. In one embodiment, there may be a strong response to energy in the spectral range of from about 150 nanometers to about 300 nanometers, from about nanometers to about 400 nanometers, from about 400 nanometers to about 430 nanometers, from about 430 nanometers to about 450 nanometers, from about 450 nanometers to about 500 nanometers, from about 500 nanometers to about 1000 nanometers, from about 1000 nanometers to about 2000 nanometers, or from about 2000 nanometers to about 3000 nanometers. In one embodiment, the photons may have a wavelength in a range of from about 160 nanometers to about 2900 nanometers, and from about 170 nanometers to about 2500 nanometers, by emitting spontaneous emission. Suitable spontaneous emissions may include photoluminescence. The crystalline composition may respond to incident energy in the spectral range of from about 150 nanometers to about 2900 nanometers. In one embodiment, the spectral range may be in a range of from about 160 nanometers to about 170 nanometers, from about 170 nanometers to about 900 nanometers, from about 900 nanometers to about 2500 nanometers, or from about 2500 nanometers to about nanometers of the stimulated emission.

The crystalline composition emission, without change or modulation by the presence of the target species, may be monochromatic light, or may be light for which the full width at half maximum (FWHM) of the emission spectrum is less than about 10% of the peak wavelength, in one embodiment. The peak emission wavelength may be greater than about 300 nanometers. In one embodiment, the peak emission wavelength may be in a range of from about 300 nanometers to about 400 nanometers, from about 400 nanometers to about 450 nanometers, from about 450 nanometers to about 460 nanometers, from about 460 nanometers to about 480 nanometers, from about 480 nanometers to about 500 nanometers, or greater than about 500 nanometers. In another embodiment, the peak emission wavelength may be in the visible light spectrum. In another embodiment, the peak emission wavelength may be in the infrared spectrum.

In one embodiment, the crystalline composition responds to interaction with a target species of a similar polarity relative to a polar surface area of the exposed surface by modulating radiation (stimulated or spontaneous); and/or, by affecting the light scatter of the radiation supplied by the radiation source. In one embodiment, the crystalline composition responds to reaction with a target species of a similar polarity relative to a polar surface area of the exposed surface by modulating radiation. In one embodiment, the crystalline composition responds to interaction with a target species of a differing polarity relative to a polar surface area of the exposed surface by modulating scattered light, a spontaneous emission, or a stimulated emission. In one embodiment, the crystalline composition responds to reaction with a target species of a differing polarity relative to a polar surface area of the exposed surface by modulating scattered light, a spontaneous emission, or a stimulated emission.

The crystalline composition may include doped material in one embodiment. The crystalline composition may have a lattice structure that is one or more of hexagonal close packed, cubic, face centered cubic, or body centered cubic. In one embodiment, the crystal lattice structure may be one or more of diamond cubic, wurtzite structure, and zinc blend structure. In one embodiment, the crystalline composition may be an epitaxially grown crystal, meaning that its crystal structure mimics that of the substrate on which it was grown. The crystalline composition may be attached to its growth substrate or, in one embodiment, may be a freestanding structure.

While reference is made separately to both the crystalline composition and to the faceted structure, the separate reference is made only help focus on inherent chemical and/or electrical properties (crystalline composition) and physical or structural features (faceted structure), and the terms are to be used interchangeably where reasonable. With reference to the above disclosed faceted structure, the faceted structure has an exposed surface. The exposed surface may have a polar surface area and a non-polar surface area. In one embodiment, the faceted structure is a truncated hexagonal pyramid having a base with a maximum diameter that is in a range of less than about 100 micrometers. If one formation method is used, the hexagonal pyramid may have a base with a maximum diameter that is in a range of from about 100 micrometers to about 15 micrometers, from about 15 micrometers to about 10 micrometers, from about 10 micrometers to about 5 micrometers, from about 5 micrometers to about 1 micrometers, or less than about 1 micrometer. The hexagonal pyramid may have a maximum height in a range of less than about 100 micrometers, from about 100 micrometers to about 50 micrometers, from about 50 micrometers to about 25 micrometers, from about 25 micrometers to about 10 micrometers, from about 10 micrometers to about 5 micrometers, or less than about 5 micrometers. If another formation method is used, the hexagonal pyramid may have a base with a maximum diameter that is in a range of from about 100 nanometers to about 75 nanometers, from about 75 nanometers to about 50 nanometers, from about 50 nanometers to about 25 nanometers, from about 25 nanometers to about 10 nanometers, or less than about 10 nanometer. The hexagonal pyramid may have a maximum height in a range of less than about 100 nanometers, from about 100 nanometers to about 50 nanometers, from about 50 nanometers to about 25 nanometers, from about 25 nanometers to about 10 nanometers, from about 10 nanometers to about 5 nanometers, or less than about 5 nanometers.

The faceted structure may be prismatic shaped; and may have no parallel sides, such as a pyramid. Although pyramids have non-parallel faces, resonance may occur between multiple, non-parallel faces. Using pyramids allows light extraction from the top of the faceted structure as opposed to the sides. This can couple light out of the exposed polar face, through the sensor layer, and into the surrounding air, vacuum, or other medium. The angle of the non-parallel faces is influenced or controlled by several factors. In one embodiment, the angle is controlled by fixing the thickness of the template layer, where thinner template layers produce relatively more platelet-like faceted structures with wall angles approaching 90 degrees perpendicular.

The faceted structure may be a hexagonal pyramid having an exposed truncated surface (e.g., about planar with the base). The truncated hexagonal pyramid may have sides that form corresponding angles with, or are off-parallel by, an angled amount in a range of less than 90 degrees. In one embodiment, the angled amount is in a range of from about 85 degrees to about 80 degrees, from about 80 degrees to about 75 degrees, from about 75 degrees to about 60 degrees, from about 60 degrees to about 50 degrees, from about 50 degrees to about 45 degrees, from about 45 degrees to about 40 degrees, from about 40 degrees to about 30 degrees, or less than about 30 degrees.

An array of the faceted structures may be included in an embodiment according to the invention. The array of faceted structures may include at least two faceted structures in a spatial relationship relative to each other. The faceted structures in the array may be spaced from each other by a distance (called the pitch) that is in a range of less than about 100 micrometers. In one embodiment, the pitch is in a range of from about 100 micrometers to about 90 micrometers, from about 90 micrometers to about 80 micrometers, from about 80 micrometers to about 70 micrometers, from about 70 micrometers to about 60 micrometers, from about 60 micrometers to about 50 micrometers, from about 50 micrometers to about 40 micrometers, from about 40 micrometers to about 30 micrometers, from about 30 micrometers to about 20 micrometers, from about 20 micrometers to about 10 micrometers, from about 10 micrometers to about 5 micrometers, from about 5 micrometers to about 1 micrometers, or less than 1 micrometer. In another embodiment, the pitch is in a range of from about 100 nanometers to about 90 nanometers, from about 90 nanometers to about 80 nanometers, from about 80 nanometers to about 70 nanometers, from about 70 nanometers to about 60 nanometers, from about 60 nanometers to about 50 nanometers, from about 50 nanometers to about 40 nanometers, from about 40 nanometers to about 30 nanometers, from about 30 nanometers to about 20 nanometers, from about 20 nanometers to about 10 nanometers, from about 10 nanometers to about 5 nanometers, or less than about 5 nanometers.

The faceted structures in the array may be oriented and disposed to be in a plane relative to a substrate that defines that plane. Alternatively, the faceted structures in the array are oriented and disposed to define an arcuate surface. If arranged as an arcuate surface the bow of the arc may be configured to provide a focal point at the detector, in one embodiment.

Figure 5:
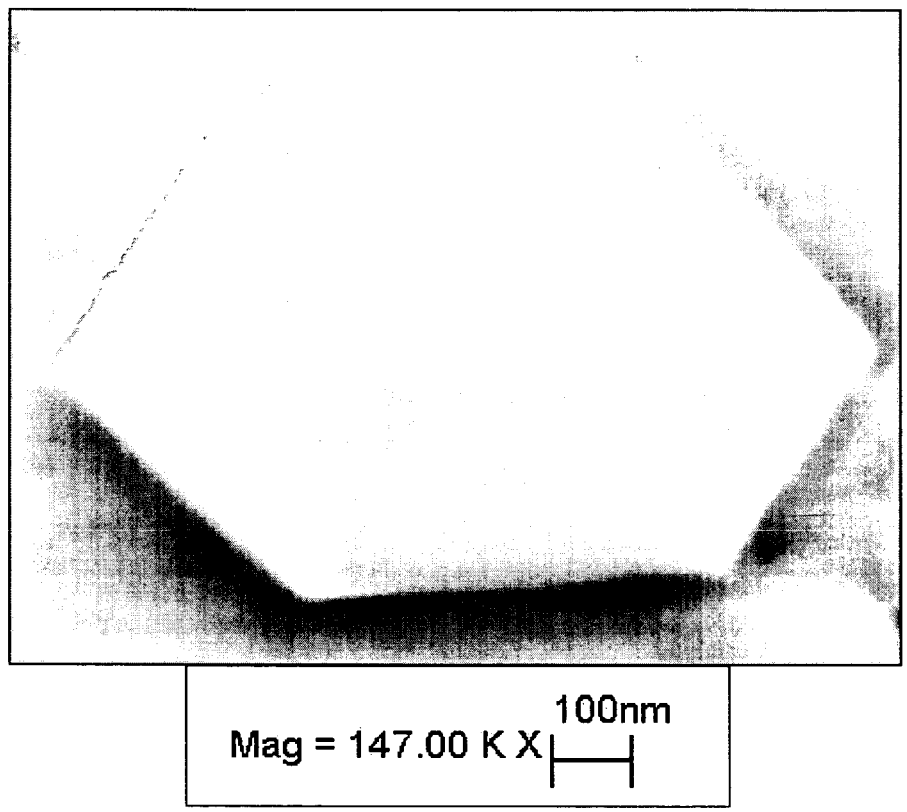
FIG. 5 is a micrograph of a faceted structure (GaN on GaN) with a naturally occurring planar face according to an aspect of the invention.

The array of faceted structures may share a common plane as shown in FIGS. 1 and 5. A planar array may allow the faceted structures to be pumped relatively evenly by the incident energy particles from the radiation source, and optical light extraction can be obtained relatively uniformly throughout the array.

In one embodiment, the array may be an ordered array such that the intercrystalline spacing or pitch (see FIG. 6) may be the same for all faceted structures in the array in two or more dimensions. Each of the plurality of faceted structures may have an identical distribution, properties, composition, size, and shape. The pitch or inter-crystalline spacing is the distance between the nearest respective facets of nearest neighbor crystal/faceted structure.

In one embodiment, this spacing may be comparable to the size of the faceted structures; that is, the intercrystalline spacing may be a multiple in a range of greater than about 0.5 times the radius of gyration of the crystal area projected onto the common plane. In one embodiment, this multiple may be in a range of from about 0.5 to about 1, from about 1 to about 2, from about 2 to about 5, from about 5 to about 10, or greater than about 10.

The faceted structures in the array may have differing properties relative to each other, and the difference may be based on the location of each of the faceted structures in the array. The differing property may be one or more the composition of the faceted structure, the size of the faceted structure, the ratio of polar surface area to non-polar surface area on an exposed surface of the faceted structure, or the sensor layer of the faceted structure. In one embodiment, the difference may include two or more of the properties. Control of the differing properties can be obtained by, for example, controlling the aperture size in the template layer. If the aperture size is a gradient over a distance, from smaller to larger, then the crystalline composition that nucleates and grows from each aperture will have properties that reflect the corresponding aperture size. As smaller crystals reach an apex, with no polar exposed face, more quickly than do larger crystals then for a single growth step, with each faceted structure having a similar or the same height, the smaller crystals will have smaller, or no, exposed surface area.

Further, the differing property from one faceted structure to another faceted structure in the array may define a gradient across the array based of the differing property. For example, the differing properties may be in the alloy content of the crystalline composition in one direction and the material or type of sensor layer in another direction. In one embodiment, the array is a multi-dimensional array. In one dimension, the faceted structure geometry may be based on the position of the faceted structure in the array, and in the other dimension, the faceted structure composition is based on the position of the faceted structure in the array.

In one embodiment, at least some of the faceted structures, or other surface-based structures, are sized and shaped to facilitate a Lotus Effect. The size, shape and pitch of the faceted structures in the array, and optionally in combination with some hydrophobic material, may be such to block polar liquid access to, and yet allow vapor access to, at least a portion of the exposed surface when contacted with a liquid and a vapor, or a liquid having a sufficiently high vapor pressure.

The faceted structure has selected opto-electronic properties. The faceted structure may form opposing charge pairs (electron-hole pairs or electron-ion pairs) in response to the energy absorbed from contact with the radiation received from the radiation source. Moreover, these pairs recombine so that photons emit. The speed at which these pairs recombine determines, in part, the mechanism of photon emission induced in the faceted structure. Where the recombination occurs quickly (e.g., on the order of tens of nanoseconds), the emission may be achieved via spontaneous emission. However, in some faceted structures the recombination may be delayed due to the existence of metastable equilibrium electron energy states in the material, creating an opportunity for emission to occur via stimulated emission mechanism. In the stimulated emission, a first photon stimulates emission of another photon of the same phase, wavelength, and direction. In one embodiment, the radiation source may create opposing charge pairs faster than they can recombine, thereby "pumping" the faceted structure into a state known as a "population inversion," where the number of opposing charge pairs in the material exceeds that found in the same material under thermodynamic equilibrium conditions.

The capability of the faceted structure to maintain a population inversion may be necessary, but not sufficient, to sustain stimulated emission in the system. Laser devices further require an optical resonant cavity, also referred to herein as an "optical resonator," to promote stimulated emission of radiation in a particular direction and to enhance the number of stimulated emission events via optical feedback. The faceted structure may confine between two reflective surfaces, such as mirrors or facets, where one surface may be completely reflective and the other surface may be partially reflective. Photons emitted in the direction promoted by the mirrors (the "optical axis") pass back and forth within the faceted structure, thereby further stimulating emission, whereas photons emitted in other directions are lost. When the number of photons produced by stimulated emission exceeds that produced spontaneously, the system can "lase," that is, produce a directional, coherent beam of electromagnetic radiation that passes through the partially reflective mirror and provides useful optical power.

The faceted structure may have a spatial dimension in the range from about 10 nanometers to about 50 micrometers. The spatial dimension, or pitch, may be in a range of from about 10 nanometers to about 50 nanometers, from about 50 nanometers to about 100 nanometers, from about 100 nanometers to about 150 nanometers, from about 150 nanometers to about 200 nanometers, from about 200 nanometers to about 300 nanometers, from about 300 nanometers to about 400 nanometers, from about 400 nanometers to about 500 nanometers, from about 500 nanometers to about 1000 nanometers, from about 1 micrometer to about 10 micrometers, from about 10 micrometer to about 100 micrometers, from about 100 micrometer to about 1 millimeter, or greater than about 1 millimeter.

In one embodiment, the faceted structure may produce stimulated emission as described above. In these embodiments, the faceted structure may include external plane faces, also referred to herein as facets (see FIG. 5). The external plane faces define an optical resonator having a dimension in a range of less than about 100 micrometers. In one embodiment, the dimensional range may be from about 10 nanometers to about 100 nanometers, from about 100 nanometers to about 1000 nanometers, from about 1 micrometer to about 25 micrometers, from about 25 micrometers, to about 50 micrometers, or greater than about 50 micrometers. The size of the resonator, in part, determines the wavelength of the radiation emitted. The resonator size may be selected to be somewhere in the range from about 0.5 times the desired wavelength to about 100 times the wavelength, to support resonance of the radiation in the desired modes. A vertical cavity surface emitting laser (VCSEL) or a resonant cavity LED (RCLED) may narrow the spectrum of excitation light and reduce off-resonance light emission. This may improve resolution and sensitivity and reduce background noise. The resonant cavity light emitting device may include a stack of group III nitride layers, including an active region. A single crystal gallium-containing nitride faceted structure on which the stack of group III nitride layers is disposed may have few or no two dimensional defects and a one dimensional defect density less than $10^5$ cm$^{-2}$. First and second mirrors define a resonant cavity inside of which the active region is disposed. Light produced by the active region resonates in the resonant cavity.

In one embodiment, the external plane faces of the faceted structure may be formed naturally upon growing the crystal, in contrast to faces formed by cleaving as-grown crystals. In such cases, the orientation of the facets may be in accordance with the crystal lattice of the medium material. As disclosed above, formed facets may have properties that distinguish and identify them relative to cleaved faces.

The faceted structure may include a potential well disposed within or upon the faceted structure. Potential wells create additional metastable electron energy states within a material by subjecting electrons and holes to quantum confinement. A potential well disposed within or upon the faceted structure may facilitate stimulated emission of electromagnetic radiation in the faceted structure by decreasing the threshold energy necessary to create a population inversion. Suitable potential wells may include quantum wells (which confine in one dimension) and quantum wires (which confine in two dimensions) within the faceted structures (which confine in three dimensions). As an example, the faceted structure may be a semiconductor crystalline composition with a diameter of a few nanometers. Because of its size, a faceted structure may confine electrons in three dimensions to a region on the order of the electrons' de Broglie wavelength in size, a few nanometers in a semiconductor.

The faceted structure may emit, via recombination of opposing charge pairs, electromagnetic radiation having a wavelength in a range of greater than about 100 nanometers. In one embodiment, the wavelength range may be from about 150 nanometers (ultraviolet) to about 10 micrometers (infrared). In one embodiment, the wavelength may be in a range from about 150 nanometers to about 180 nanometers, from about 180 nanometers to about 380 nanometers, from about 380 nanometers to about 400 nanometers, from about 400 nanometers to about 500 nanometers, from about 500 nanometers to about 1 micrometer, from about 1 micrometer to about 2 micrometers, or greater than about 2 micrometers.

The wavelength of the radiation emitted by crystalline composition may be selected by material choice, and by controlling the size and shape of faceted structure comprising the crystalline composition. The wavelengths of radiation emitted by luminescent materials may be determined in large part by their electron energy band structures, which may be known or may be readily calculated. Moreover, where resonance plays a role, as it does in stimulated emission, the wavelength may depend on crystal geometry. The optical resonators are sized to coincide with a whole number of half-wavelengths allow for the greatest optical resonance, and this encourages optical modes to resonate and leave the crystalline composition/faceted structure.

In one embodiment, the faceted structure may emit electromagnetic radiation having a plurality of wavelengths. As the wavelength emitted by a particular crystalline composition may be a function of crystalline composition, size, shape, crystal structure, and the like. Because the crystalline composition is an emitter, embodiments of the invention provide an opportunity to combine multiple wavelengths of emission from an array of faceted structures with differing crystalline compositions from one faceted structure to another faceted structure. In one embodiment, the faceted structures in the array differ from each other in at least one characteristic selected from one or more of size, shape, crystal structure, and chemical composition.

As disclosed above, the crystalline composition has an exposed surface defined by a peripheral edge that opposes the base surface, and a plurality of side surfaces. A sensor layer may be disposed on the exposed surface and/or the side surfaces, or within the exposed surface to a depth that allows for optical or electronic interaction with the corresponding surface. For embodiments in which the sensor layer is within the surface of the crystalline composition, infusion of the sensor layer components can be performed during the formation of the faceted structures.

The sensor layer may react with, or interact with, a target species when the target species is sufficiently proximate to the sensor layer. The sensor layer responds to the reaction or to the interaction in a detectable manner. The exposed surface may have at least a portion that is covered by a sensor layer. The sensor layer responds to contact with a target species by modulating a generated spontaneous emission or stimulated emission of the crystalline composition. In addition, the sensor layer may respond further by modulating or changing, in a detectable manner, one or more of an electrical, acoustic or viscoelastic, or magnetic response of the crystalline composition.

The sensor layer may be polymeric, inorganic, organic, composite, nanocomposite, formulated, biomolecular, biotissue, solid, porous, liquid (for example ionic liquid). In one embodiment, the sensor layer may function while immersed in a fluid medium, such as blood, lymph, bile, or insulating oil. In one embodiment, the sensor layer may include one or more capture agent or binder. As discussed further herein, the capture agent or binder may interact or react with the target species. The sensor layer may be a catalyst layer.

A suitable catalyst layer may include a simple metallic layer or series of metallic layers. The catalyst layer, in one embodiment, may be a sensor layer, and may be capable of selectively binding and/or interacting with certain kinds of chemicals, proteins, nucleic acids, gases, or vapors. The catalyst layer, if present, is in electrical communication with one or more contact metallization layers.

In one embodiment, the sensor layer includes a catalyst in an amount in a range of greater than about 0.001 part per billion (ppb). In one embodiment, the sensor layer includes a catalyst in an amount in a range of from about 0.001 ppb to about 0.001 ppb, from about 0.001 ppb to about 0.01 ppb, from about 0.01 ppb to about 0.1 ppb, or from about 0.1 ppb to about 1 ppb. The sensor layer may include the catalyst in an amount in a range of greater than about 1 ppb. In one embodiment, the catalyst content may be present in an amount in a range of from about 1 ppb to about 10 ppb, from about 10 ppb to about 100 ppb, from about 100 ppb to about 200 ppb, from about 200 ppb to about 500 ppb, from about 500 ppb to about 1000 ppb, from about 1000 ppb to about 5000 ppb, or greater than about 5000 ppb.

In one embodiment, all, or almost all, of the sensor layer is the catalyst. In one embodiment, the sensor layer includes a catalyst in an amount in a range of from about 75 percent to about 85 percent, from about 85 percent to about 90 percent, from about 90 percent to about 95 percent, or about 95 percent to about 99 percent. Other embodiments include amounts of catalyst in ranges therebetween the foregoing. Of note is that the relative amount of catalyst is affected by the balance of material in the sensor layer—those embodiments having little or no supporting matrix have relatively large amounts of catalyst, while those sensor layers that have additional materials and supporting matrices have relatively lower amounts of catalyst. Further, the sensor layer may include pendant metallic and/or nitrogen atoms capable of interacting or of reacting with the target species. The sensor layer may be a continuous layer, or may have portions of discontinuity. In one embodiment, the sensor layer is a mono-layer. In another embodiment, the sensor layer has a thickness that is in a range of from about 1 nanometer to about 10 nanometers, from about 10 nanometers to about 50 nanometers, from about 50 nanometers to about 500 nanometers, or greater than about 500 nanometers.

A sensor layer component for selectively interacting with, or reacting with, the target species may be incorporated in the sensor layer. The sensor layer component may be chemically attached to the sensor layer material such that a functional group responsible for the selective interaction with the target species may be free to undergo this interaction or reaction. Such a functional group may be a moiety on the sensor layer component or a part of the sensor layer component molecule that offers a determined steric configuration for accepting a target species having a complementarily shape and/or property.

The sensor layer component may be a cell, or part of a cell, so that its membrane may be used to recognize a biotarget species. An example of an interaction, or reaction, may be that between an enzyme and a corresponding protein. A suitable sensor layer component can be a single stranded nucleic acid, or aptamer, folded into a specific conformation and sensitive to a variety of target species. Other sensor layer components may include antibodies, proteins, peptides, small molecules, and the like. In one embodiment, the sensor layer component may include a nucleic acid sequence. An associated dye may include a fluorescence-quencher pair, a pH active dye, an ion-sensative dye (preferably in situations where there is conjugation with an antibody), and chelator conjugated antibodies, with cleavable or non-cleavable linkers, which can form fluorescent chelates (e.g., lanthanide chelates). Other suitable sensor layer components may include one or more of cleavable linker disulfides (cleaved by reducing agents), alkoxysilane (cleaved by halides), photochemical agents (cleaved by light), and alkylsulfone (cleaved by basic materials).

As disclosed above, the sensor layer may include one or more sensor layer components. The sensor layer components, while including the catalysts above, may include also a capture agent or a binder. The capture agent or binder interacts or reacts with the target species. In one embodiment, the capture agent interacts with the target species. In one embodiment, the capture agent reacts with the target species. In one embodiment, the binder interacts with the target species. In one embodiment, the binder reacts with the target species. The capture agent or binder may include one or more of an antibody, antibody fragment, protein, peptide, aptamer, or biologically active small molecule. In one embodiment, the capture agent or binder may include a nucleic acid.

The capture agent or binder may have a binding affinity in a range of greater than about 1 KDa. In one embodiment, the binding affinity may be in a range of from about 1 KDa to about 5 KDa, from about 5 KDa to about 10 KDa, from about 10 KDa to about 20 KDa, from about 20 KDa to about 50 KDa, from about 50 KDa to about 75 KDa, from about 75 KDa to about 100 KDa, from about 100 KDa to about 125 KDa, from about 125 KDa to about 150 KDa, from about 150 KDa to about 175 KDa, from about 175 KDa to about 185 KDa, from about 185 KDa to about 200 KDa, or greater than about 200 KDa.

The sensor layer has an average thickness of less than 100 micrometers. In one embodiment, the average thickness is in a range of from about 100 micrometers to about 90 micrometers, from about 90 micrometers to about 80 micrometers, from about 80 micrometers to about 70 micrometers, from about 70 micrometers to about 60 micrometers, from about 60 micrometers to about 50 micrometers, from about 50 micrometers to about 40 micrometers, from about 40 micrometers to about 30 micrometers, from about 30 micrometers to about 20 micrometers, from about 20 micrometers to about 10 micrometers, from about 10 micrometers to about 5 micrometers, from about 5 micrometers to about 1 micrometers, or less than 1 micrometer.

In one embodiment, the sensor layer components may include a chromophore attachment moiety, a chromophore-targeting moiety, a chromophore probe, and the like. Suitable chromophore attachment moieties may include albumin, transferrin, fatty acid binding proteins, globulins, red blood cell components, lyphocytes, stem cells, antibodies, and lipoproteins; as well as polylysine and polysaccharides. Suitable chromophore-targeting moieties may include a thiol or disulfide group. Suitable chromophore probes may include a Cy5.5, Cy5 and Cy7; IRD41 and IRD700; NIR-1 and IC5-Osu; Alexflour 660, Alexflour 680, LaJolla Blue; FAR-Blue, FAR-Green One, and FAR-Green Two; ADS 790-NS and ADS 821-NS. Other suitable probes may include indocyanine green and analogs, indotricarbo cyanine, and chelated lanthanide compounds.

For securing the sensor layer component to a sensor layer, or in the sensor layer, the sensor layer component may be retained in pores of the sensor layer material or to the sensor layer surface. The retention may be by, for example, one or more of surface tension, molecular weight, affinity, chemical fixation, or configuration. Other sensor layer components may be secured to the expose surface by adsorption, covalent bonding, or entrapment in a matrix. The sensor layer component may be mixed with a suitable solvent or matrix having a low vapor pressure before impregnating into the pores of the sensor layer to inhibit the escape of the sensor layer component and to increase the shelf life of the sensing element. Depending on the nature of the target species suspected to be present, the solvent or matrix may be chosen to promote or enhance the solubilization of the target species therein. For example, a hydrophobic solvent or matrix may be used for hydrophobic target species, and hydrophilic solvent or matrix for hydrophilic target species.

The outer surface of the sensor layer may include a molecular imprinted polymer. Suitable molecular imprinted polymers may be conductive polymers. In one embodiment, cavities in the outer surface are tailored to correspond to particular target species, such as ligands, using one or both of shape and functional groups. Washing with solvents between uses can remove the target species from the cavities and ready the sensor layer containing the molecular imprinted polymer for reuse.

In one embodiment, the sensor layer has an outward facing surface, and disposed on at least a portion of the outward facing surface is an exclusion layer. The exclusion layer may be a size excluding layer, a selective chemical exclusion layer, and/or a non-target species exclusion layer. The exclusion layer may selectively exclude, prevent contact with, or protect, the sensor layer based on determined criteria. The exclusion may be based on one or more characteristic of the target species (allowing it to pass) or of the non-target species (preventing contact with the sensor layer). Selective exclusion may be based on one or more of size, polarity, affinity, hydrophobicity, conformation or configuration, phase, and the like. A zeolyte, microporous, and/or mesoporous layer may exclude based on pore size relative to the size of the target species. In one embodiment, the exclusion layer may be a porous or a perforated structure. In another embodiment, the exclusion layer may be a lipid bilayer. A lipid bi-layer may exclude based on polarity, or protein content, for example. A Lotus-effect structured surface may prevent liquid from contact, but may allow for vapor or gas-phase contact. An expanded microporous membrane, e.g., e-PTFE, may be surface treated and used as the exclusion layer. In one embodiment, a polymeric exclusion layer may be polymerized onto the sensor layer. Suitable polymeric exclusion layers may include polypyrrole, polythiophene, polyaniline, or polyacetylene.

A suitable exclusion layer may be mesoporous or microporous. Mesoporous may have an average pore size in a range of less than about 1000 nanometers. Microporous may have an average pore size in a range of greater than about 1000 nanometers. In one embodiment, the average pore size is a bimodal distribution having both mesoporous and microporous pores. The pore size may be selected based on determined factors. Such factors may include the desire to obtain a reasonably rapid diffusion or permeation rate of the target species into and through the exclusion layer. Other factors may include the use of size exclusion affects to preclude reaction or interaction of non-target species with the sensor layer component.

The average pore size may be selected to have one or more narrow size distributions. For mesoporous exclusion layers, suitable average pore sizes may be in a range of from about 1 nanometer to about 10 nanometers, from about 10 nanometers to about 25 nanometers, from about 25 nanometers to about 75 nanometers, from about 75 nanometers to about 100 nanometers, from about 100 nanometers to about 250 nanometers, from about 250 nanometers to about 500 nanometers, from about 500 nanometers to about 750 nanometers, or from about 750 nanometers to about 1000 nanometers. For microporous exclusion layers, suitable average pore sizes may be in a range of from about 1 micrometer to about 10 micrometers, from about 10 micrometers to about 25 micrometers, from about 25 micrometers to about 75 micrometers, from about 75 micrometers to about 100 micrometers, from about 100 micrometers to about 250 micrometers, from about 250 micrometers to about 500 micrometers, from about 500 micrometers to about 750 micrometers, from about 750 micrometers to about 1000 micrometers, or greater than about 1000 micrometers.

In one embodiment, a passivation layer may be applied to one or more surfaces of the faceted structure. In one embodiment, the passivation layer is less than about five atomic layers. In another embodiment, the passivation layer is less than three atomic layers. Examples of materials suitable for use as the passivation layer, alone or in combination, include, $TiO_2$, $SiO_2$, and $Al_2O_3$. The passivation layer may affect, change, modulate or decrease a signal relative to the sensor layer, that emanates from the faceted structure during use. The signal difference may be characterized as relatively stronger emission intensity via the sensor layer or as an altered (shorter or longer) excited state lifetime.

The sensor layer component may associate with the target species, that is, the material desired-to-be-detected or the analyte of interest. The association may be in equilibrium (an electronic interaction) or may be a chemical bonding (a bond forming reaction). For the purposes of this disclosure, ligand formation and complexing is considered chemical bonding unless context or language indicates otherwise. The target species, or multiple target species, that is desired to be detected influences the selection of the sensor layer. In various embodiments the target species may include one or more of metal ion, protein, living cells or cell parts, tissue, virus, bacteria, fungus and mold, prion, vapors, and gases (such as gaseous fire products, gaseous exhaust products, and mine environmental gas (e.g., methane)). In one embodiment, the target species may include a chemical warfare agent and/or a biological warfare agent. Suitable chemical warfare agents may include one or more incapacitating agents, lacrymators, vesicants or blister agents, nerve agents, pulmonary agents, blood agents, and malodorants.

Suitable incapacitating agents may include nervous system affecters, vomiting agents, choking agents, hallucinogens, sedatives, narcotics, depressants, and the like, and combinations of two or more thereof. In one embodiment, an incapacitating agent may include 3-quinuclidinyl benzilate (QNB, BZ), which may be an anticholinergic agent that may react with a sensor layer comprising, for example, choline. Alternative nervous system affecters may include commercially available over the counter (OTC) or prescription pharmaceutical compositions. In one embodiment, an incapacitating agent may include curare, or a curare analog or derivative.

Suitable lacrymators may include one or more of o-chlorobenzylmalonitrile, chloromethyl chloroformate, stannic chloride, sym-dichloromethyl ether, benzyl bromide, xylyl bromide, methyl chlorosulphonate, ethyl iodoacetate, bromacetone, bromomethyl-ethyl ketone, acrolein (2-propanal), capsaicin including analogs and derivatives, or the like.

A suitable vesicant may include one or more of sulfur mustard, nitrogen mustard, or an arsenical such as Lewisite. Suitable sulfur mustard may include one or more of 2-chloroethyl chloromethyl sulfide, bis(2-chloroethyl) sulfide or dichloroethyl disulfide, bis(2-chloroethylthio) methane, 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl) ether, or bis(2-chloroethyl thioethyl) ether. Suitable nitrogen mustard may include one or more of bis(2-chloroethyl) ethylamine, bis(2-chloroethyl) methylamine, or tris(2-chloroethyl)amine. Suitable Lewisites may include one or more of 2-chlorovinyl dichloroarsine, or bis(2-chlorovinyl)chloroarsine, tris(2-chlorovinyl) arsine.

Suitable nerve agents may include cholinesterase inhibitors. In one embodiment, a cholinesterase inhibitor may include one or more of o-alkyl (Me, Et, n-Pr or i-Pr)-phosphonofluoridates, such as o-isopropyl methylphosphonofluoridate (sarin) or o-pinacolyl methylphosphonofluoridate (soman); o-alkyl N,N-dialkyl (Me, Et, n-Pr or i-Pr) phosphoramidocyanidates, such as o-ethyl N,N-dimethyl phosphoramidocyanidate (tabun); or o-alkyl S-2-dialkyl (Me, Et, n-Pr or i-Pr)-aminoethyl alkyl (Me, Et, n-Pr or i-Pr)

phosphonothiolates and corresponding alkylated or protonated salts, such as o-ethyl S-2-diisopropylaminoethyl methyl phosphonothiolate (VX).

Suitable pulmonary agents may include one or both of phosgene (carbonyl chloride) and perfluroroisobutylene. Suitable toxins may include one or more of palytoxin, ricin, saxitoxin, or botulinum toxin.

Suitable blood agents may include forms of cyanide such as salts, and analogs and derivatives of cyanide salts. A suitable solid salt of cyanide may include sodium, potassium, and/or calcium. A suitable volatile liquid form of cyanide may include hydrogen cyanide and/or cyanogen chloride.

In one embodiment, the sensor layer component reacts and/or interacts with one or more spoilage indicators associated with microbial by-products. By-products associated with spoiled fish may include, for example, one or more amine. Suitable amines may include one or more of histamine, trimethylamine, dimethylamine, ammonia, and the like.

In one embodiment, the sensor layer component reacts and/or interacts with meat spoilage indicators, such as associated microbial by-products. Suitable meats include beef, lamb, pork, chicken, and the like. For example, the sensor layer component may be reactive with, or interactive with, one or more biogenic diamines, cadaverine or histamine, that is formed by the biological activity of bacteria in contact with meat. The spoilage factor, and diamine content, may be directly linked to the bacterial content of spoiled meat. In one embodiment, sensor may be reactive with, or interactive with, the decarboxylation of free amino acids on and in the meat by enzymes released by spoilage microorganisms. Two of these products, putrescence and cadaverine, may have a distinctive odor and may the odor concentration may correlate with surface bacteria counts. The surface bacteria count may be used to evaluate meat freshness.

In one embodiment, a surface of the faceted structure may be employed to contact a fluid sample, where the fluid is a liquid. An exemplary liquid sample is blood, and suitable target species may include one or more of proteins, albumin, urea, uric acid, lactate dehydrogenase, alkaline phosphatase, alanine transferase, aspartate transferase, gamma globulin transferase, bilirubin, cholesterol, ferritin, triglyceride, saccharides, phosphoenol pyruvate, amylase, creatinine, or creatinine kinase. Suitable saccharides may be mono- or poly- and include sugars such as glucose, sucrose, fructose, sucralose, lactose, galactose, and ribose. Other suitable target species may include one or more of potassium ions, sodium ions, calcium ions, chloride ions, or inorganic phosphate ions.

Toxic vapors such as benzene, chloroform, toluene, and any other used as degreasing agents and processing agents, Suitable target species that are a gas include one or more of NO, $NO_2$, $NH_3$, $CO_2$, CO, and $H_2$. Other suitable gaseous target species include one or more of alcohols, such as methanol, ethanol, or propanol; or aromatic groups, such as benzene or styrene. Still other suitable gaseous target species include one or more aromatic species, such as benzene, toluene, or styrene. Any of the foregoing may be halogenated, such as chloroform. Other low molecular weight organic molecules are suitable, and organic molecules of any molecular weight with reactive functional groups such as hydroxyl, silanol, allyl, vinyl, epoxy, ether, carboxy, and the like. Suitable non-organics include sulfur-containing, heavy metal-containing, halogen-containing, and silicon-containing materials. In one embodiment, suitable target species may include one or more of ammonia, acetone cyanohydrin, arsenic trichloride, carbonyl sulfide, chloroacetone, chlorine trifluoride, formaldehyde, ethylene dibromide, hydrogen bromide, methyl bromide, dimethyl sulfate, methyl isocyanate, ethyl chloroformate, nitric acid, phosphorus oxychloride, iron pentacarbonyl, sulfuryl chloride, isopropyl isocyanate, sulfur dioxide, trifluoroacetyl chloride. Yet other suitable gaseous (including dissolved gases) target species may include halogens, such as bromine, fluorine, or chlorine.

Gas target species are particular useful where the sensor layer components, or the sensor layer itself, is a catalyst material. In one embodiment, gaseous target species are identifiable by one or more characteristic including polarity, dipole moment, molecular size, corresponding sensor layer component, and the interaction or reaction of any two or more of the foregoing. For example, a gaseous mixture of ethanol and toluene may interact with a faceted structure having a polar surface and a non-polar set of surfaces in the manner of the ethanol interacting with the polar surface, and the toluene interacting with the non-polar surfaces. The interaction with the polar surface may affect, modulate or change, for example, the stimulated emission from the faceted structure, while the interaction with the non-polar surface (e.g., side surfaces of the faceted structure) affect, modulate or change, for example, the spontaneous emission or the scattering of radiation from the radiation source as reflected or refracted off of the faceted structure side surfaces. In one embodiment, a dual channel sensing technique allows for multiple sensing methods for one or more target species at the same time or sequentially.

The substrate may be a foundation of epitaxial growth. Substrate layers can be a single crystal, quasi-single crystal, or poly crystalline. Suitable substrates may include sapphire, $SiO_2$, SiC, ZnO, AlN, GaN, InN, AlGaN, InGaN, AlInGaN, or lithium gallate. The substrate may resist degradation in a "harsh" environment having one or more of increased pressure, increased temperature, or reactive chemicals. The substrate has a first surface, and the crystalline composition may be disposed or grown on the first surface. The substrate may be ceramic, or may be a ceramic-coated metal. One or more electrical leads or circuits may be encased by the ceramic or ceramic coating. The substrate may be a crystalline material in one embodiment. The substrate may transmit radiation though the substrate and to the crystalline composition. The transmitted radiation can interact with the crystalline composition to be changed in a detectable manner in the presence of the target species reacted or interacted with the sensor layer component. The substrate may transmit the changed transmitted radiation through the substrate.

With regard to the substrate, single crystal and quasi-single crystal each refer to a crystalline structure that may have a relatively high crystalline quality, with a reduced number of defects. Single crystal includes material where the atoms form a uniform periodic array. A quasi-single crystal may have a predetermined range of crystal defects, for example, less than about 10,000 defects per square centimeter, or about $10^{16}$ defects per cubic centimeter. Polycrystalline material includes a plurality of randomly oriented grains where each grain may include a single crystal.

Crystal defects refers to one or more of point defects, such as vacancies, interstitials, and impurities; one-dimensional linear defects, such as dislocations (edge, screw, mixed); two-dimensional planar defects, such as tilt boundaries, grain boundaries, cleavage points and surfaces; and three-dimensional extended defects, such as pores, and cracks. Defect may refer to one or more of the foregoing unless context or language indicates that the subject is a particular subset of defect. Free of tilt boundaries means that the single crystal may have tilt boundaries at an insubstantial level, or with a tilt angle such that the tilt boundaries may not be readily detectable by TEM or X-ray diffraction; or, the crystal may include tilt boundaries that are widely separated from one another, e.g., by at least 1 millimeters or by a greater, specified distance.

The substrate may have an average thickness of less than about 100 micrometers. In one embodiment, the substrate may have an average thickness in a range of from about 20 nanometers to about 50 nanometers, from about 50 nanometers to about 100 nanometers, from about 100 nanometers to about 150 nanometers, from about 150 nanometers to about 200 nanometers, from about 200 nanometers to about 300 nanometers, from about 300 nanometers to about 400 nanometers, from about 400 nanometers to about 500 nanometers, from about 500 nanometers to about 1000 nanometers, from about 1 micrometer to about 10 micrometers, from about 10 micrometer to about 100 micrometers, from about 100 micrometer to about 1 millimeter, or greater than about 1 millimeter.

Other suitable layers may be present. A backside contact metallization is a structural layer that may act as a reflector and/or as an electrical contact layer. Backside metal can be any metal or conductive and/or reflective film. The template layer is an epitaxial layer or other deposited layer that rests on the substrate. Contact metallization layers 1 & 2—Contact metallization may establish an electric contact to the faceted structure. This layer can contact the substrate, template layer, catalyst layer, or intermediate layer directly.

In one embodiment, an isolation layer may be placed between facets or cleavage surfaces, or between areas on the exposed face of the crystalline composition or faceted structure. Alternatively, the isolation layer can separate portions of the face or facet of the crystalline composition from neighboring materials and/or surroundings. The isolation layer may be electrically insulating, and suitable isolation layer materials may be dielectric. In one embodiment, the isolation layer may include one or more of $SiO_2$, SiN, TiO, TiN, TaO, or aluminum oxide. In one embodiment, a contact separation layer may be placed between facets or cleavage surfaces, or between areas on the exposed face of the crystalline composition or faceted structure. The contact separation layer may prevent unwanted electrical conduction pathways between contact metallization layers or between one or more metallization layers and other layers.

The portion of the substrate that is exposed, for example, the portion not covered by a faceted structure or a template layer, may be coated for protection of the substrate. In one embodiment, the coating may have a low surface energy so as not to impede transport of target species to the sensor layer.

An apparatus or system according to one embodiment of the invention may include an article that includes the substrate, the faceted structure disposed on the substrate, and the sensor layer disposed on a facet or cleavage surface of the faceted structure. The faceted structure is disposed on the first surface. The faceted structure has an exposed surface, and the exposed surface has peripheral edge defining a diameter of the exposed surface. The sensor layer is disposed on the exposed surface, in which the sensor layer is operable to react or to interact with a target species when the target species is sufficiently proximate to the sensor layer, and the sensor layer is capable of responding to the reaction or to the interaction in a detectable manner. The system may further include a detector unit. The detector unit may detect a response to the reaction or to the interaction of the target species with the sensor layer.

The substrate may be the same as disclosed hereinabove insofar as the substrate resists degradation in an environment of increased pressure, increased temperature, or reactive chemicals, wherein the substrate has a first surface. The substrate may transmit radiation though the substrate and to the faceted structure. The transmitted radiation can interact with the faceted structure to be changed, modulated, or changed and modulated in a detectable manner in the presence of a target species reacted or interacted with the sensor layer. The substrate may transmit the changed, modulated, or changed and modulated transmitted radiation back through the substrate.

The detector may detect a stimulated emission of radiation that has been changed, modulated, or changed and modulated by the interaction of the target species with the sensor layer component. Suitable detectors may include a photomultiplier or a charge coupled device. These components may be used in combination with a scintillation material. In one embodiment, the detector may include one or both spectroscope for time domain fluorescence (FLIM) and fluorescence resonance energy transfer (FRET). Fluorescent radiation may be characterized in terms of intensity, spectrum, or temporal properties. In one embodiment, fluorescence lifetime imaging may be conducted in both the time domain and/or in the frequency domain. In time-domain FLIM, a pulsed laser source may be the radiation source used for excitation and the fluorescence emission decay may be sampled, using a time-gated detector, at various delays following the excitation pulse. For frequency-domain measurements, the intensity of a continuous wave laser excitation radiation source may be sinusoidally modulated and so generate a correspondingly modulated fluorescence emission. The lifetime may be calculated from the phase shift or the fall in modulation depth of the fluorescence signal relative to the excitation signal.

FRET (Fluorescence Resonance Energy Transfer) may be used to measure, for example, proteins interactions. At least two different sensor layer components are fluorescent molecules (fluorophores) that are fused with corresponding sensor layer component binders with affinities for a particular protein, peptide, or the like. Regular (non-FRET) fluorescence occurs when the first fluorophore absorbs electromagnetic radiation from the radiation source of one wavelength (the excitation frequency) and re-emits that energy at a different wavelength (the emission frequency). For the combined FRET effect, the emission peak of the first fluorophore (the donor) must overlap with the excitation peak of the other fluorophore (the acceptor). By a long-range dipole-dipole coupling mechanism, the excited state donor nonradiatively transfers energy to the acceptor. The excited acceptor emits light at its own emission wavelength. The net result is that the donor emits less energy than it normally would (since some of the energy it would radiate as light gets transferred to the acceptor instead), while the acceptor emits more light energy at its excitation frequency (because it is getting extra energy input from the donor fluorophore). Where FRET is used in accordance with an embodiment of the invention, at least two differing fluorophore sensor layer components are disposed in the sensor layer within about 20' to about 100' (0.002 micrometers to 0.01 micrometers) of each other.

A suitable fluorophore pair for FRET is cyan fluorescent protein (CFP)-yellow fluorescent protein (YFP) pair. Additional examples of commercially available materials that may form suitable FRET pairs are listed in Table 1.

TABLE 1

Suitable examples of FRET fluorophore pairs

| Donor | Acceptor |
|---|---|
| Fluorescein | Tetramethylrhodamine |
| IAEDANS | Fluorescein |
| EDANS | Dabcyl |
| Fluorescein | Fluorescein |
| BODIPY FL | BODIPY FL |
| Fluorescein | QSY 7 and QSY 9 dyes |

Suitable detectors may include a photomultiplier (PM) tube or a charge coupled device (CCD). In one embodiment, the CCD is an eight-bit video rate intensified CCD camera commercially available from ISIS-III, Photonic Science, Ltd. (East Sussex, England).

While some embodiments generate electromagnetic radiation by luminescence, for example, some other embodiments include an apparatus that has a radiation source. During operation, the radiation source may generate and direct radiation to the faceted structure. The supplied radiation is of sufficient quantity and of a type capable of eliciting a stimulated emission, a spontaneous emission, or both types of emission from the faceted structure. For example, the radiation source may be an ultraviolet laser. If an array of faceted structures is present, the radiation source may scan back and forth across the array.

The radiation source provides one or more of photons, protons, electrons, neutrons, beta particles, or alpha particles. The photons may be provided at a wavelength in a range of greater than about 10 nanometers. In one embodiment, the wavelength range may be in a range of from about 50 nanometers (ultraviolet) to about 10 micrometers (infrared). In one embodiment, the wavelength may be in a range from about 10 nanometers to about 100 nanometers, from about 100 nanometers to about 1 micrometer, from about 1 micrometer to about 10 micrometers, from about 10 micrometers to about 100 micrometers, or greater than about 100 micrometers.

In one embodiment, the radiation source may be a source of electrons, such as a wire-wound filament emitter (e.g., made of a refractory material such as tungsten), a field emitter, a dispenser cathode, a photo-emitter, or a ferroelectric cathode. Electrons may be emitted from the radiation source and may be received by the collector across a gap defined by surfaces of the radiation source and the collector. The gap may be of sufficient size to support a high electric field between the radiation source (which may be referred to as a "cathode") and the collector (which may be referred to as an "anode"). Electrons may be accelerated across the electric field to impinge upon the collector and the emission medium. The voltage used to create the field may be in the range from about 1 kilovolt (kV) to about 10 kV.

The system includes a controller in communication with the radiation source and the detector. The controller may initiate the radiation source to direct radiation to the faceted structure. After the supplied radiation contacts one or more faceted structure, the faceted structure responds by emitting a detectable energy. The detector may detect the emission and subsequently generate a signal based on the emission. The controller may then receive the signal generated by the detector based on the faceted structure emission.

In the presence of the target species, the sensor layer modulates the emission. That is, the target species may interact with, or react with, the sensor layer to modulate or detectably change the emission. The detector signal differs based on whether the emission is modulated or is not modulated. In one embodiment, the degree of modulation, the type of modulation, or both the degree and type of modulation are detectable. If the degree and/or type of modulation are detectable, the detector generates a corresponding signal that communicates the difference.

The controller determines whether the target species is present based on a difference in the detector signal (modulated or not modulated). In one embodiment, the controller further determines additional information (beyond mere presence) of the target species based on, for example, the degree and/or type of modulation. The larger the degree of modulation, for example, the larger the concentration of the target species.

The apparatus or system may include a housing and a power source in communication with the detector. The apparatus or system may be a portable unit. That is, the housing may be sized and configured so as to be carried and/or mounted; and, the power unit may be similarly sized and configured to be mobile during use. Increased power consumption needs, or larger arrays may make a stationary unit desirable, thus the system can be configured with relatively large power needs, high volume throughput, and/or decontamination facilities as a stationary unit.

The apparatus may operate in a partial vacuum or at a reduced pressure where "reduced" is less than ambient. Trace amounts of gas may contact the sensor layer in such an embodiment during use, which may be detected by the detector. The apparatus may operate at a temperature in a range of greater than about room temperature. In one embodiment, the operating temperature may be in a range of from about 25 degrees Celsius to about 50 degrees Celsius, from about 50 degrees Celsius to about 100 degrees Celsius, from about 100 degrees Celsius to about 150 degrees Celsius, from about 150 degrees Celsius to about 175 degrees Celsius, from about 175 degrees Celsius to about 200 degrees Celsius, from about 200 degrees Celsius to about 225 degrees Celsius, from about 225 degrees Celsius to about 250 degrees Celsius, from about 250 degrees Celsius to about 500 degrees Celsius, from about 500 degrees Celsius to about 600 degrees Celsius, from about 600 degrees Celsius to about 700 degrees Celsius, from about 700 degrees Celsius to about 800 degrees Celsius, or greater than about 800 degrees Celsius. Embodiments of the apparatus may operate in gas. Embodiments of the apparatus may operate while submersed in liquid.

In one embodiment, a detection method includes directing radiation to a faceted structure capable of responding to the radiation by one or both of a stimulated emission or a spontaneous emission. The stimulated emission or the spontaneous emission may be modulated in the presence of a target species. The modulation of the stimulated emission or the spontaneous emission may be detected. And, detection of the modulation may indicate the presence of the target species. In one embodiment, detection of the magnitude or type of the modulation may indicate quantitatively the concentration or the amount of the target species present. Quantitative measurements may be based further on such values as standard modulation values (e.g., regression analysis), surface area of the faceted structure, type of sensor layer, and the like.

A matching crystal lattice should allow the epitaxial growth of a crystalline composition on an intermediate layer (not shown). For electron-pumping, the intermediate layer may electrically conduct to at least some extent, to minimize heating and to prevent charging effects. For light extraction, a low index of refraction may be desirable in the support layer to reduce optical coupling of light into the support layer and to encourage optical resonance. As an example, for an $Al_{0.15}Ga_{0.85}N$ nanocrystal array, an n-doped $Al_{0.25}Ga_{0.75}N$ epitaxial layer may be a suitable support material because the intermediate material may be lattice-matched to $Al_{0.15}Ga_{0.85}N$, may be thermally and electrically conductive, and may have a significantly lower index of refraction than the $Al_{0.15}Ga_{0.85}N$ nanocrystal array.

The intermediate layer may mitigate stresses due to mismatches in coefficient of thermal expansion and lattice mismatch. The intermediate layer may be a nucleation layer for growth of the faceted structure array. In one embodiment, multiple intermediate layers may be applied to reduce stress. Examples of materials suitable for use as the intermediate layer include one or more of aluminum nitride, gallium-containing nitride, indium nitride, aluminum indium gallium-containing nitride, silicon, zinc oxide, gallium arsenide, aluminum indium gallium arsenide, lithium gallate, and boron nitride. The intermediate layer may be deposited on the substrate using chemical or physical vapor deposition processes. The intermediate layer may have a thickness in the range from about 10 nanometers to about 100 nanometers, from about 100 nanometers to about 1 micrometer, from about 1 micrometer to about 10 micrometers, from about 10 micrometers to about 100 micrometers, or greater than about 100 micrometers.

The substrate may include an electrically insulating material, such as sapphire, quartz, silicon dioxide, silicon nitride, aluminum nitride, or a metal oxide material. Where the substrate may be insulating, a conductive path may be established from the support layer, through the substrate, and to a conductive portion of the device by a conductive via or metallization pattern. Alternatively, the substrate may conduct a charge, such as a semiconductor or electrically conducting material.

Figure 2:
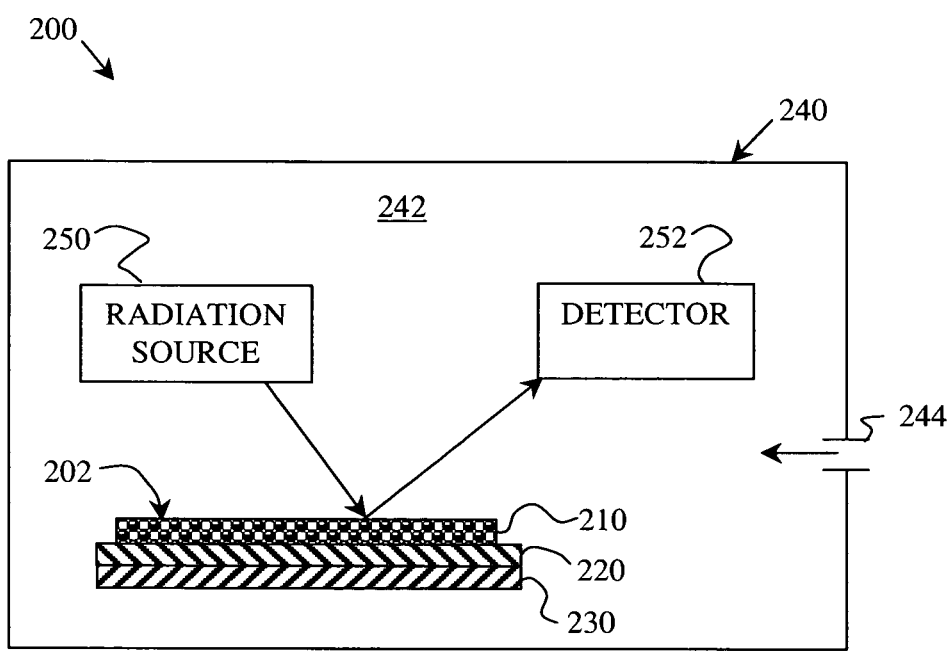
FIG. 2 is a schematic representation of an exemplary device according to an embodiment of the invention.

FIG. 2 illustrates a schematic example of a sensor device 200 in accordance with embodiments of the invention. The device includes a sensor assembly 202. The sensor assembly includes a faceted structure array 210 disposed on a substrate 220. The faceted structure array includes a template layer 230 supporting the faceted structure array. The faceted structure array may include one or more faceted structures. A housing 240 has a wall that defines a chamber 242 and an aperture or inlet 244 for an amount of sample to enter the chamber. In the chamber, or alternatively in communication with the faceted structure array through a window (not shown), are a radiation source 250 and a detector 252.

Figure 3:
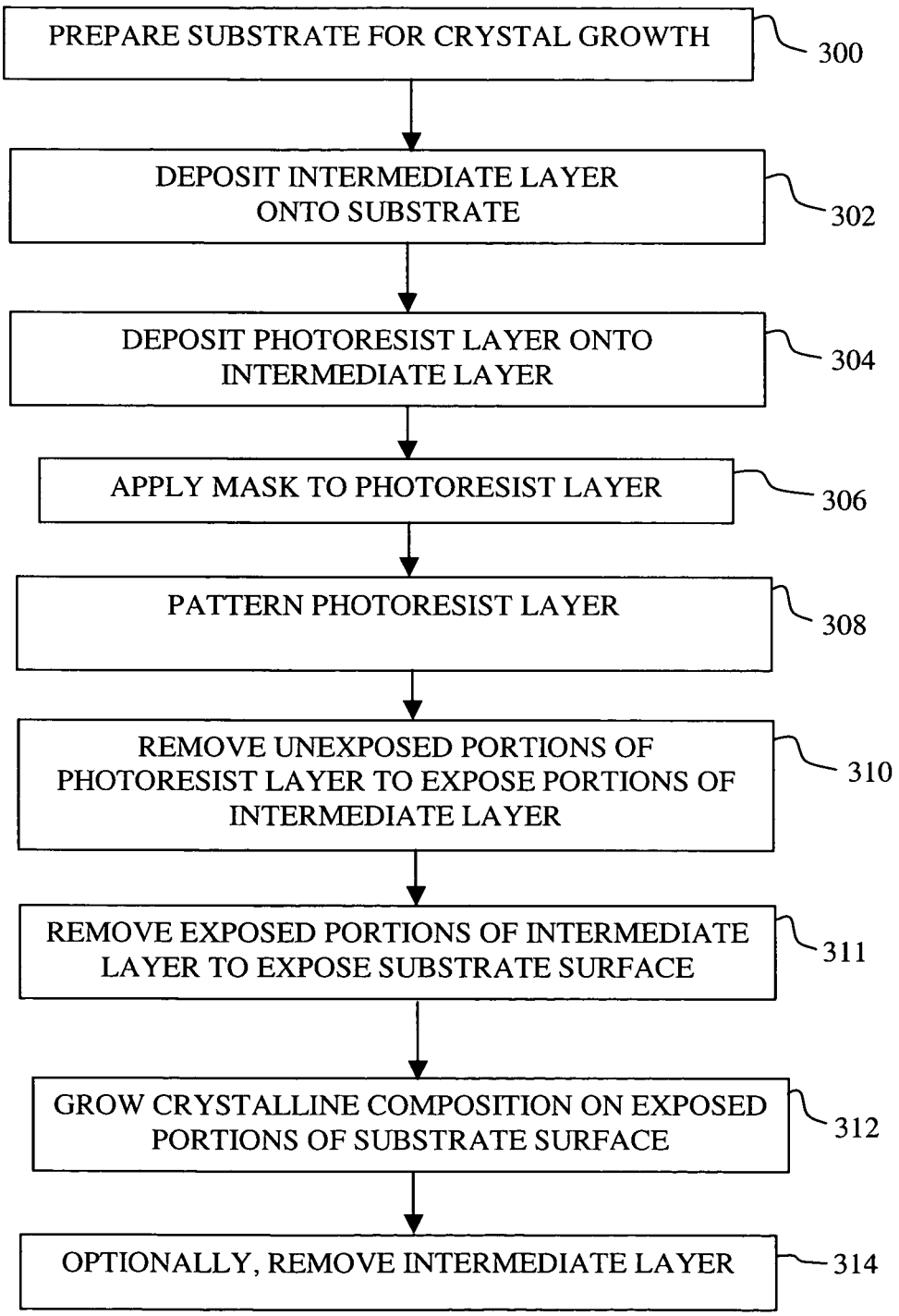
FIG. 3 is a flow diagram representing a method according to an embodiment of the invention.

FIG. 3 illustrates an exemplary process for providing a patterned mask on the substrate. A substrate is prepared for crystal growth (300). An intermediate layer is deposited on the substrate by sputtering or chemical vapor deposition (302). A photoresist layer is disposed or coated onto the intermediate layer (304). A mask is attached to the photoresist layer (306). The mask should be stable in the environment present during the crystal growth process. The patterned mask may be applied to the substrate surface so that only selected areas of the substrate are exposed. The mask shields certain areas of the substrate so that no crystal growth will occur in masked regions during subsequent steps.

The photoresist layer is patterned (308) using photolithographic techniques. Such techniques include UV lithography, electron beam lithography, or contact lithography. The photoresist layer is selectively removed from the unexposed regions (310), for example by a solvent wash, and the mask may be removed. In one embodiment, the exposed portions of the intermediate layer, which correspond to the unexposed portions of the photoresist layer, may be in a size range of from about 0.1 micrometers to about 0.3 micrometers, from about 0.3 micrometers to about 0.7 micrometers, or greater than about 0.7 micrometers. The intermediate layer is then selectively etched while masked with the photoresist layer, the photoresist layer is then removed. This leaves a substrate with surface portions masked by the intermediate layer. The masked substrate may be exposed to a crystal growth process, such as, for example, metallorganic chemical vapor deposition (MO-CVD) such that crystals grow only in the exposed regions of the substrate. In one embodiment, the crystalline composition may be grown epitaxially on the substrate, which allows the crystal structure to be controlled in part via selection of the substrate. The exposed portions of intermediate layer may be removed to expose at least a portion of the substrate surface (311). The faceted structures are grown on the areas of the substrate surface layer where the intermediate layer was removed (312). After growth, the intermediate may be removed, leaving behind the substrate with the crystals disposed on the substrate surface (314).

The size and shape of the faceted structure determines, in part, what wavelength(s) of radiation may emit. Crystal growth parameters used in the growth process affect the faceting, and hence the shape, of the resultant crystals. Process parameters include temperature, precursor flow rates, pressure, and growth time. Moreover, the selection of the substrate in an epitaxial growth process affects faceting during crystal growth due to strains associated with lattice mismatch between the substrate and the crystalline composition materials. For example, gallium-containing nitride crystals grown with no or low mismatch strain exhibit pyramidal morphologies, while highly strained crystals show prismatic shapes. The shape of the crystals may be controlled to provide the desired optical properties required for embodiments of the invention.

Figure 4:
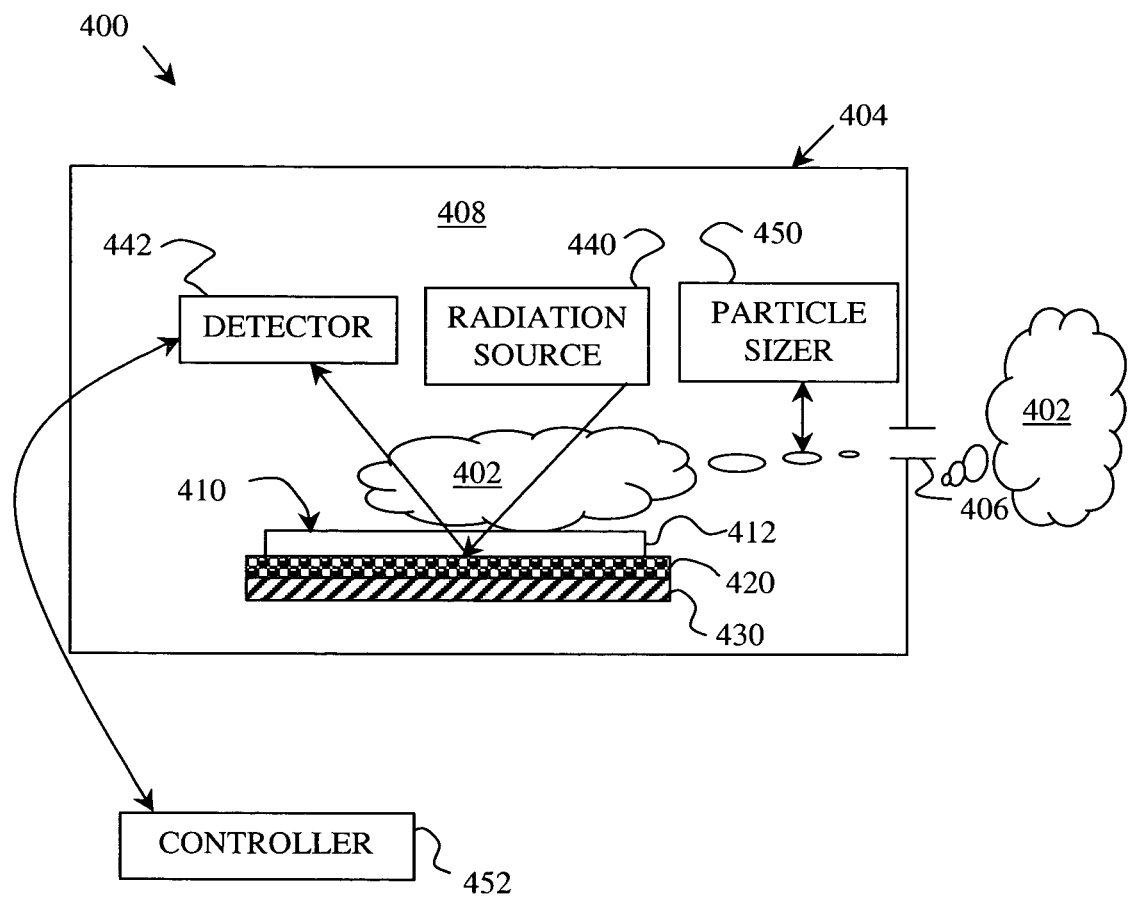
FIG. 4 is a schematic representation of a fluorescence detector in accordance with embodiments of the invention.

An exemplary aerosol fluorescence detector 400, such as a bioaerosol fluorescence detector, is illustrated in part in FIG. 4. During use, an atmospheric sample 402 flows into a housing 404 through an inlet 406 and into a chamber 408, which is defined by an interior surface of the housing. The bioaerosol may contain one or more target species and one or more non-target species. The bioaerosol, one in the chamber, contacts a sensor device 410. The sensor device includes an exclusion layer 412 disposed on a sensor layer 420. The sensor layer 420 is supported by a substrate 430 having an array of faceted structures disposed thereon (not shown) and supporting the sensor layer. As indicated by directional arrows, an energy beam is generated by a radiation source 440, and is directed to the sensor layer through the exclusion layer. The exclusion layer is transparent to the wavelength of the energy beam. The energy beam is in the UV or blue range and causes fluorescence in the faceted structures in the array. The target species crosses the exclusion layer by one or more of diffusion, ion pump, or protein transport. Non-target species are excluded from contact with the sensor layer by rejection at the exclusion layer based on one or more of size, polarity, or protein specific affinity. After contact of the target species with the sensor layer components, the emitted luminescent light is captured by the detector 442. The detector is an array of photodiodes and/or CCDs. At the same time, particulate sizing and velocity information may be derived using a laser-based Aerodynamic Particle Sizing (APS) and/or High Volume Aerodynamic Particle Sizing (HVAPS) device 450. A controller 452 communicates with the detector, and optionally also with the particle sizer and the radiation source.

When the sensor layer components are nucleic acids, the covalent or ionic bonds between the sensors and the surface are stable from about 0 degrees Celsius to about 100 degrees Celsius. The surface to which the sensor layer components attach may be an excitation source. The surface of the faceted structure excitation source may be bare, in which case the sensor layer components are covalently or ionically bound directly to the faceted structure surface. Alternatively, the surface of the faceted structure surface may be coated (by, for example, gold) or by a matrix (such as sol-gel) that is bound to the faceted structure surface. In which case, the sensor layer components are covalently or ionically bound to the coating or matrix.

Figure 6:
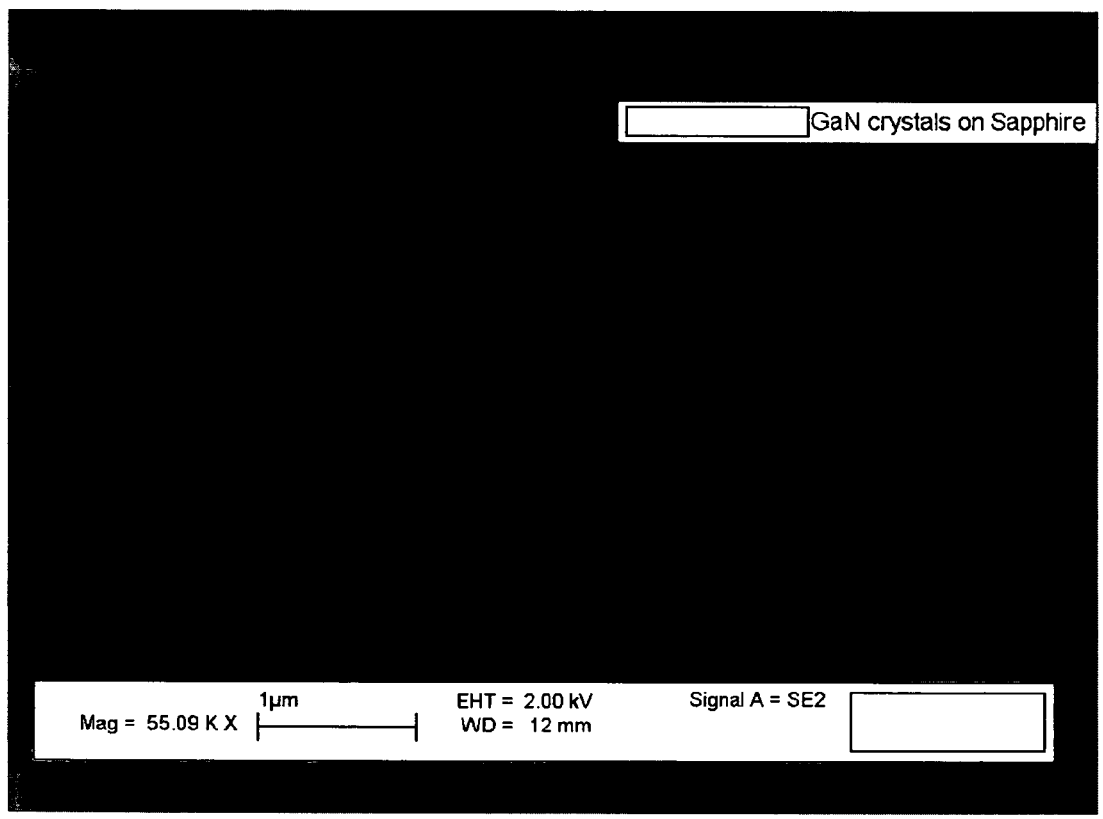
FIG. 6 is a micrograph of a faceted structure array (GaN on sapphire) with naturally occurring planar faces according to an aspect of the invention.

FIG. 5 is a micrograph of a crystalline composition formed as a faceted structure in accordance with an embodiment of the invention. The faceted structure has an exposed planar face that is substantially parallel with a plane defined by the supporting substrate. The exposed face is polar. Both the crystalline composition and the substrate include gallium-containing nitride. FIG. 6 is a micrograph of a two-dimensional array of faceted structures that include gallium-containing nitride and that are formed on a sapphire substrate. The amount of the catalyst that forms the sensor layer disposed on the exposed polar planar face varies in amount and type according to the position of the faceted structure in the array.

Figure 7:
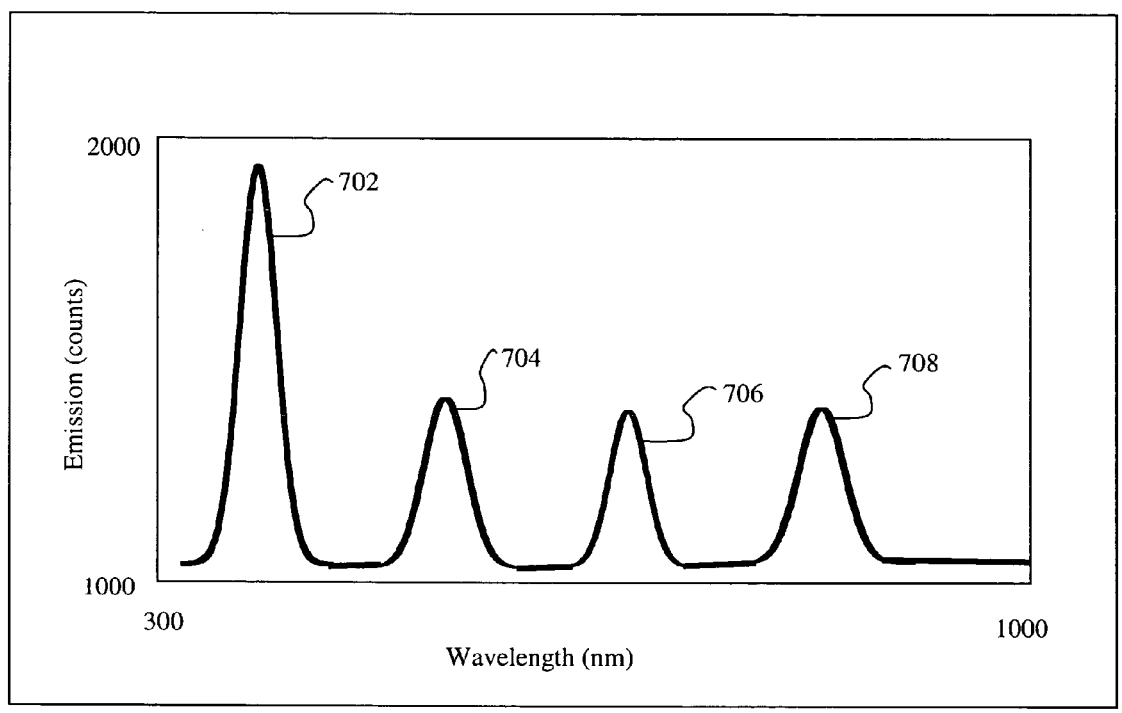
FIG. 7 is a graph illustrating an emission difference in wavelength during exposure to a sample including a first target species, a second target species, and a third target species.
Figure 8:
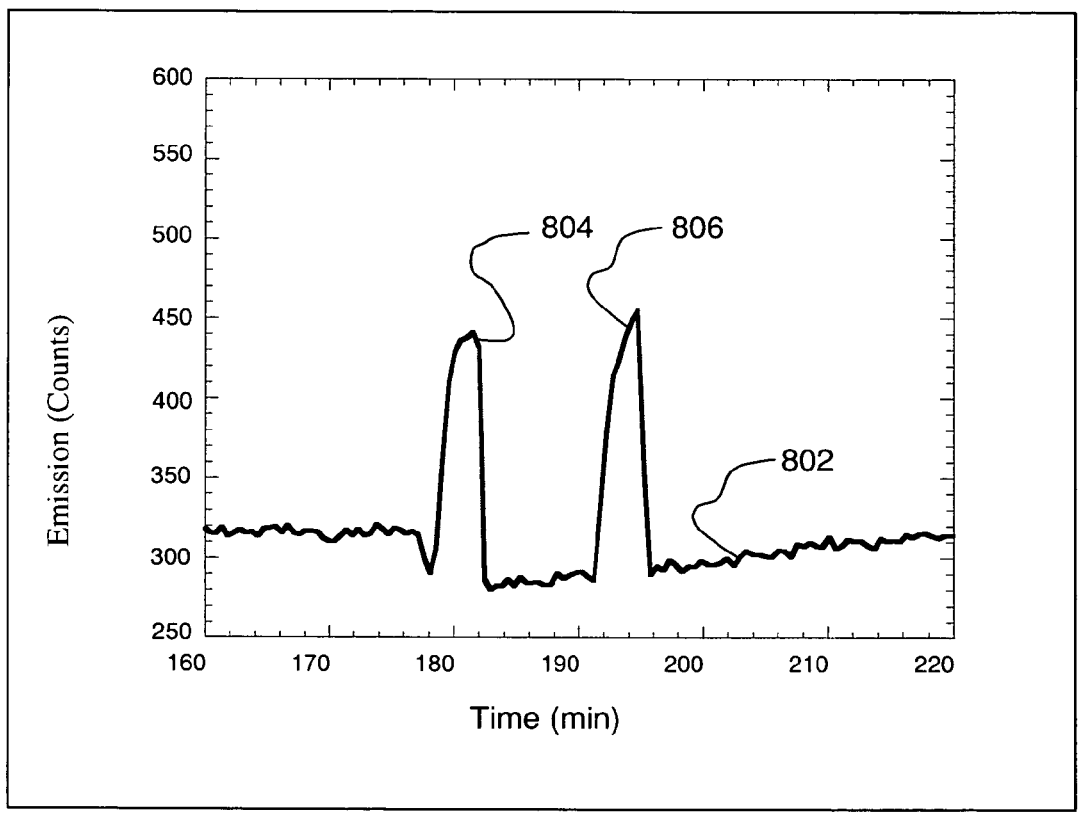
FIG. 8 is a graph illustrating stimulated emission upon two exposures to a target species over time.
Figure 9:
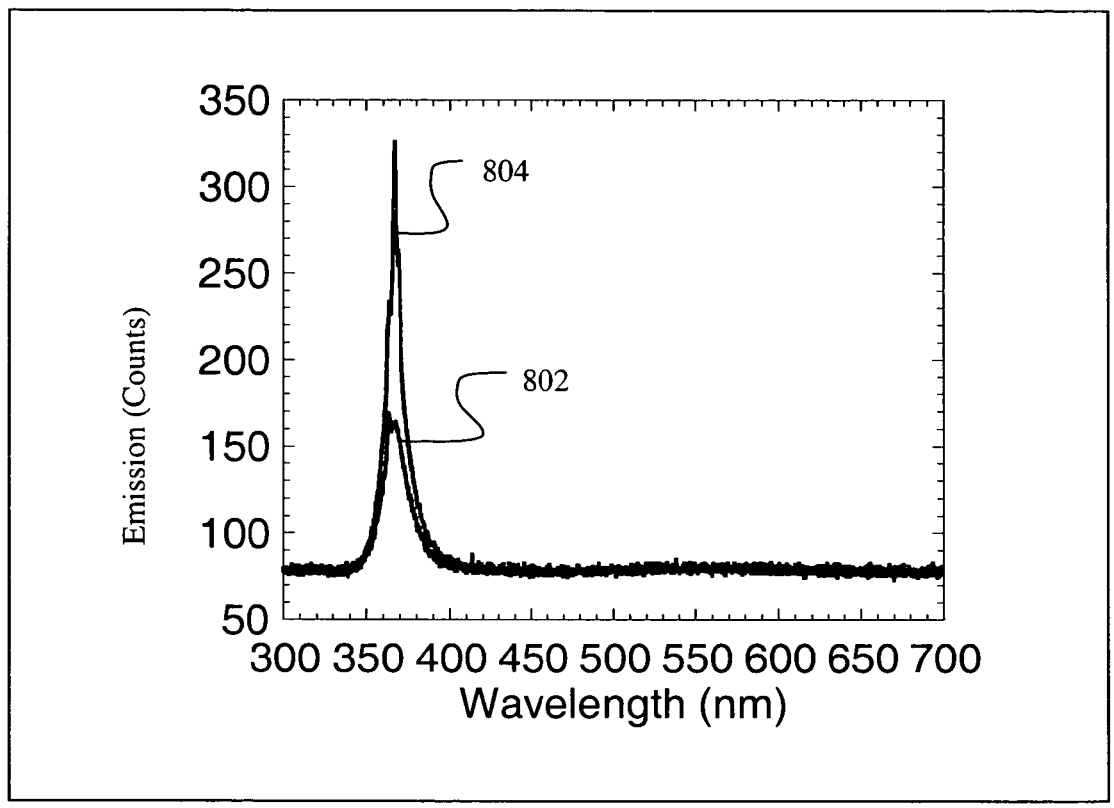
FIG. 9 is a graph illustrating stimulated emission one of the peaks shown in FIG. 8 at a particular wavelength.
Figure 10:
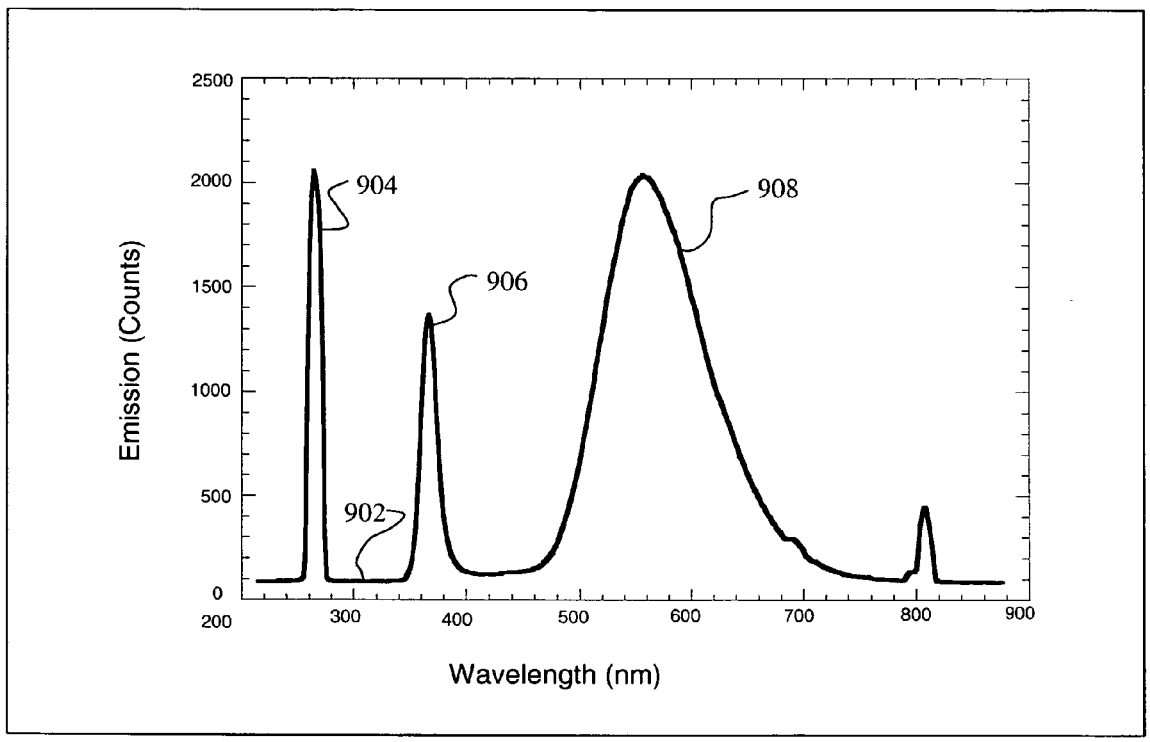
FIG. 10 is a graph illustrating detected peaks at differing wavelengths, where the peaks correspond to scattered light, stimulated emission, and spontaneous emission; and subgraphs illustrating each of the peaks with regard to alternating exposures to differing target species.
Figure 11:
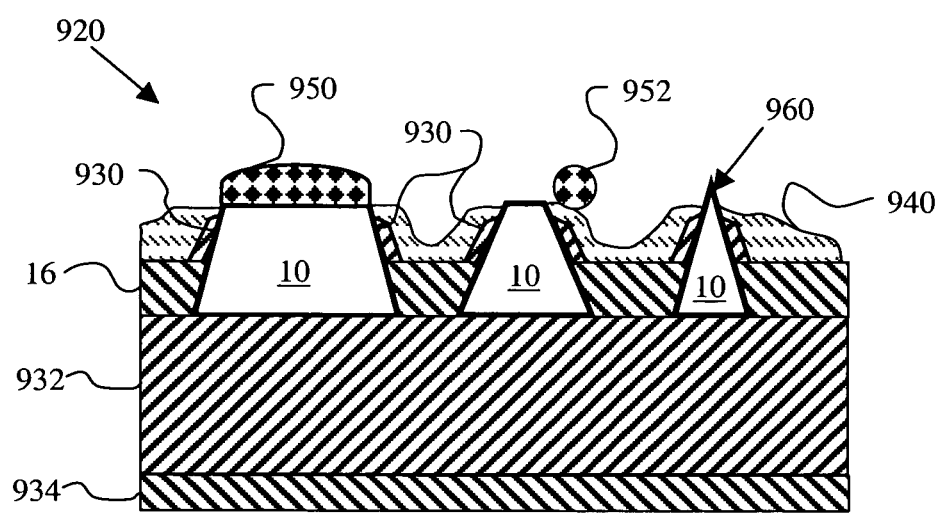
FIG. 11 is a schematic representation of an array of faceted structures having each differing polar surface areas and the effect of the surface area relative to one or more inherent properties of a target species.

With reference to FIG. 7, a graph shows the shift or modulation of wavelength for emission spectra of a faceted structure in contact with a sample containing three differing target species and corresponding sensor layer components. A baseline peak 702 is indicative of the stimulated emission of the faceted structure in response to irradiation by the radiation source (e.g., an ultraviolet light source). Three differing target species, bound to corresponding sensor layer components, each initiate the generation of light at a larger wavelength relative to the baseline peak. The peaks 704, 706, 708 represent light at wavelengths indicative of the presence of the corresponding target species. The light wavelength is formed by modulating the stimulated emission of the faceted structure in the instance of the each of the peaks 704, 706, and 708. Other types of optical modulations or wavelength shift mechanisms may be used in other embodiments.

For example, if a target species (e.g., nucleic acid) is present in the sample, and if the target species binds to the sensor layer components on the faceted structure to form DNA, RNA or RNA/DNA hybrids, then the luminophores will emit light, or will emit light that differs detectably from the light that the luminophore emits when the target species is not bound to the sensor layer components. Luminophores include chromophores, fluorophores, phosphors, and chemilumophores.

The luminophores (or complexes of luminophores and intercalator-type agents) may be introduced as free floating in the sample solution, or may be bound to the sensor layer. When the sensor layer components and the target species react or interact with each other to form a target species-component complex, the luminophores associate with the target species-component complexes. In one embodiment, the luminophores are bound to the sensor layer. In an alternative embodiment, the luminophores (or luminophore-intercalator complexes) are tethered to the sensor layer. In this alternative embodiment, the luminophores are tethered to the surface via relatively flexible molecules (e.g., alkyl chains) that are long enough to allow the luminophores to associate with the target species-component complex.

If the target species is ssDNA, an ssDNA sensor layer component may be bound to a surface of the faceted structure. Surface attachment of the ssDNA sensor layer component may be achieved by sputter coating the surface with gold and by tethering the ssDNA sensor layer component to the gold coating via thiolated ends on the ssDNA sensor layer component. The faceted structure with the tethered ssDNA sensors can be placed in a buffer solution containing ssDNA target species and an appropriate luminescent dye bound to an intercalator agent. When the ssDNA target species and the ssDNA sensor layer component hybridize to form a duplex, the dye associates with the duplex via intercalation or groove binding, which alters the conformation of the dye. The conformation altering causes the dye to luminesce when excited by light emitted by the faceted structure or from the radiation source. The luminescence can be detected by a photodetector.

When the target species binds to form a duplex (e.g., DNA/RNA hybrid) between the sensor layer component and the target species, a luminophore (e.g., SYBR Green I) luminesces at 520 nm, which can readily be detected by eye, CCD camera, or photodetector. Examples of other luminophores that can indicate duplex formation include: intercalator dyes; ruthenium polypyridyl dyes; cyanine dyes; dyes based on phenanthridine, acridine, indole or imidazole structures; and other DNA/RNA stains such as silver stain.

EXAMPLES

The following examples are intended only to illustrate methods and embodiments in accordance with the invention, and as such should not be construed as imposing limitations upon the claims. Unless specified otherwise, all ingredients are commercially available from such common chemical suppliers as Alpha Aesar, Inc. (Ward Hill, Mass.), Spectrum Chemical Mfg. Corp. (Gardena, Calif.), Thomas Scientific, Inc. (Swedesboro, N.J.), and the like.

Example 1

Article Fabrication

An article is fabricated by disposing a plurality of faceted structures onto an anode of a scanning electron microscope (SEM). A microscope cathode (radiation source) provides a source of electrons to pump the medium of the device. The plurality of faceted structures define a 1 millimeter by 1 millimeter planar array of gallium-containing nitride crystalline compositions epitaxially grown on an aluminum nitride template layer disposed on a sapphire substrate. The faceted structures are hexagonal prisms or pyramids, each having a nominal base size of about 700 nanometers. The array has a pitch, or a nominal intercrystalline spacing, of about 700 nanometers. Each faceted structure is electrically connected to a grounded anode plate by a copper conductor. A fiber optic probe connects to a spectrometer and monitors emission from the faceted structure as electrons from the SEM cathode impinged upon the faceted structure. Accelerating voltage of the SEM controls the energy of the electrons.

Example 2

Sensor Layers

Four arrays of faceted structures (Samples 1, 2, 3 and 4) are prepared as in Example 1 except on a sapphire substrate having back metallization rather than an SEM anode. The faceted structures are arranged in an array that is two dimensional and planar (see FIG. 6). The exposed facet of the truncated faceted structures differs from one portion of the array to another portion of the array (X-Y direction) such that the ratio of polar surface area to non-polar surface area is based on the position of the faceted structure in the array. The exposed facets are polar c-plane naturally occurring planar faces.

Onto each of the exposed facets of sample 1 are disposed a sensor layer that includes a catalyst component. In this instance, the catalyst includes a metal, and particularly a catalyst component that interacts with ethanol. In the presence of ethanol, the sensor layer mass changes the strain and/or electrical properties of the surface of each faceted structure. The sensor layers have differing amounts of catalyst across the array in the X-Z direction. The metal catalyst is applied by sputtering to a thickness that is determined by the desired catalyst amount. Particularly, the catalyst amount/concentration defines a gradient (X-Z) from about 0.01 ppm to about 1 ppm in concentration across the array.

Onto each of the exposed facets of sample 2 are disposed a sensor layer that includes an antibody component. In this instance, the antibody component is selective for avian influenza. The sensor layers have differing amounts of the antibody across the array in the X-Z direction. The antibody component is covalently reacted to a prepared surface of the polar faceted structure exposed surface using a linker. Particularly, the amount of the antibody component is determined by the amount of the linker reacted to the exposed surface, but the amount forms a concentration gradient (X-Z) across the array.

A luminophore is attached to the faceted structure surface in sample 2. The antibody component and luminophore emit light when stimulated by the emission of the faceted structure when in the presence of the avian influenza virus. That is, the avian influenza virus reacts with the antibody, and in the presence of the luminophore, the light emitted from the faceted structure to which the sensor layer is attached either stimulates the luminophore, or is modulated by the chemluminescent light from the luminophore-antibody-avian influenza virus hybid.

In sample 3, a catalyst component is applied as in sample 1 and an antibody component is applied as in sample 2. The linker is layered over the catalyst component, and the antibody component is layered over the linker with the luminophore.

Sample 4 is the same as sample 2, except that Bovine Spongiform Encephalitis (BSE) prion is the target species, and the antibody component is specific for BSE rather than avian influenza virus.

Each of the samples 1-4 is placed in a housing, and is oriented to face a radiation source and a detector. The housing includes an inlet for a test sample that may contain an amount of target species. Initially, a baseline is determined by flashing radiation from the detector to the faceted structure array, causing the faceted structure array to emit radiation of characteristic wavelength(s) at a characteristic intensity as the radiation beam is directed to particular locations in the array. The controller, which directs the radiation source, notes the amount of supplied radiation, the portion of the array to which the radiation is directed, and the response from the detector. The baseline is stored for future use. Optionally, testing conditions can be measured, and differing testing conditions can establish corresponding baselines.

Testing is performed by flowing one or more test samples into the housing to contact the faceted structure arrays. For sample 1, the test sample is one of a series of test samples. Some of the test samples have ethanol, some have a long chain polyol (polyethylene glycol, mw>500), and some have no hydroxyl moiety. For sample 2, the test sample is one of a series of test samples. Some of the test samples have living avian influenza virus, some have crippled or dead avian influenza virus, some have an unrelated, innocuous viral component, and some have no viral component. For sample 3, a flowing stream of test sample is applied to the faceted structure array. At one time, ethanol is injected into the test sample flow to contact the faceted structure array, and later avian influenza virus is injected into the flow, and later still a mixture of both ethanol and avian influenza virus is injected into the flow. Sample 4 is tested in a similar manner to sample 2, but uses BSE.

The result for sample 1 is that a distinct wavelength emission is detected by the detector after contacting the sample of ethanol to the array, no such peak is observed when no ethanol is contacting the sensor layer, and a peak at a differing wavelength is observed when the polyethylene glycol is contacting the sensor layer. Accordingly, the differing alcohols can be present, and are distinguishable from each other. Further, the amount of ethanol determines the peak height of the response detected. In one instance, the quantity of ethanol is determined by linear regression against known concentration samples with regard to the test conditions/baseline. In another instance, the threshold value of ethanol present in the sample is too low for some of the faceted structures in the array to generate a signal but is present in sufficient quantity to generate a detectable signal on those faceted structures that have a larger exposed surface and more catalyst deposited thereon. Thus, extrapolation allows for concentration determination, within a defined concentration range, without the need for linear regression.

The result for sample 2 is that a distinct wavelength emission is detected by the detector after contacting the sample containing the avian influenza virus to the array, no such peak is observed when no avian influenza virus is contacting the sensor layer, and no corresponding peak is observed when the other viral components are contacting the sensor layer. Accordingly, the differing viral materials are distinguishable from each other.

For sample 3, the ethanol peak is detected, the avian influenza virus is detected, but after the avian influenza virus reacts with the sensor layer additional measurements do not prove to be conclusive. The interaction of the alcohol is weak enough to allow for reset of the sensor layer with dilution or flushing, but the covalent bonding of the avian influenza virus forms a relatively durable bond with the sensor layer.

The result for sample 4 is that a distinct wavelength emission is detectable by the detector after contacting the sample containing the BSE to the array, no such peak is observed when no BSE is contacting the sensor layer, and no corresponding peak is observed when the other components are contacting the sensor layer. Accordingly, the differing materials are distinguishable from each other.

Example 3

Exclusion Layers

Several arrays of faceted structures (samples 4-6) are prepared as in Example 2 Sample 1 with the exception that AlGaN is used rather than GaN. Over the sensor layer of each array an exclusion layer is deposited. For sample 4, a sol-gel process sets up a mesoporous frit having pores that are sized to be larger than ethanol but smaller than hexanol, in diameter and that are hydrophilic due to residual hydroxyls.

In sample 5, Lotus Effect layer is coated over the sensor layers. The Lotus Effect layer has both microscale structures, and nanoscale structures disposed on the microscale structures, that are hydrophobic and bound to the faceted structure array surface by a porous binder material. The structures are spaced from each other to provide the desired hydrophobic affect.

Surface hydrophilization using thermal oxidation in a dry atmosphere allows the deposition of highly mobile lipid membranes by vesicle fusion. In sample 6, a lipid bilayer is disposed over a carboxylic acid group, the carboxylic acid group itself is bound in the sensor layer. The sensor layer is bound to the polar exposed surface. Particularly, a polymeric monolayer is formed from a monomer that is a derivative of dimyristoylphosphatidylethanolamine (DMPE), polyethyleneglycol (PEG), and a triethoxysilane group (for covalent linkage to the acid group on the sensor layer). That is, the polymeric monolayer is formed on the outer surface of the sensor layer having an acid functional group. A supported bilayer is formed by the addition of 1.1 ml of 100 μM lipid vesicles. The lipid vesicles spread on and fuse the supported monolayer. After 2 hours of equilibration at room temperature, excess unfused vesicles are flushed with 5 volumes of buffer. Lipid bilayer spanning proteins are selected to transport the target species across the bilayer that would otherwise exclude like materials.

1) Blanks, 2) aliquots of water and target species bacteria, and 3) aliquots of material containing a mixture of polar organic molecules, inorganic ions, and bacteria as the target species are introduced to the faceted structure array. The lipid bilayer-excluded substances do not contact the sensor layer as indicated by detector readings that are about the same for the aliquots with and without polar molecules and ions.

Example 4

Detection

An article comprising an array of faceted structures is produced according the method of Example 1, except that the substrate is c-plane gallium nitride, the faceted structure has an exposed planar surface that is polar and oriented as the substrate surface, and a metal catalyst sensor layer is sputtered over the exposed planar surface. The metal catalyst interacts with ammonia.

A stream of purified dry air flows across the article surface to contact the sensor layer. A radiation source provides ultraviolet radiation to the faceted structures that emit stimulated light in response at a base line indicated by reference number 802. FIG. 8 is a graph illustrating stimulated emission upon two exposures to a target species over time. At about 178 minutes and about 192 minutes, 5 percent by volume anhydrous ammonia gas is injected into the flow of air to contact the sensor layer. The first peak 804 illustrates the increase in stimulated emission at a wavelength of about 360 nanometers for the first amount of ammonia gas, and the second peak 806 illustrates the second amount of ammonia gas. After the flow of air purges the ammonia, the stimulated emission at the wavelength declines back to about baseline. The ammonia interacts, but does not react with, the metal catalyst sensor layer.

FIG. 9 is a graph illustrating stimulated emission of the first peak 804 shown in FIG. 8 at a wavelength of about 360 nanometers. The first peak 804 is in addition to the emission counts from the baseline.

Example 5

Multi-Channel Detection

An article is prepared as in Example 4, except that a bare exposed surface is used and no metal catalyst is used. That is, the sensor layer includes only the functional polar groups of the exposed planar surface. A baseline flow of air is contacted to the article surface, and the sensor layer in particular, to form a baseline emission 902 in response to radiation supplied at a wavelength of about 270 nanometers. Alternating amounts of gaseous ethanol and toluene are introduced to the sensor layer. FIG. 10 is a graph illustrating detected peaks at differing wavelengths, where the first peak 904 corresponds to scattered light, and the second peak 906 corresponds to stimulated emission near the band edge. The third peak 908 corresponds to spontaneous emission, due primarily to defects within the faceted structure. It is therefore possible to extract multiple data sets by the differing interaction mechanisms of the target species. Here the two target species are separately polar or non-polar, and thus interact with either the correspondingly polar or non-polar surfaces of the faceted structure.

In addition, when the target species are alternated, the peaks corresponding thereto alternate. That is, the scattered light peak rises in the presence of the toluene, and an ethanol presence increases the stimulated emission peak. The spontaneous emission peak remains constant regardless of target species, which allows for a baseline for quantification or concentration determinations. The toluene may interact with the non-polar sides of the faceted structure, and the presence of the target species affects/increases the scatter/reflection (peak 904) off the faceted sides. The ethanol may react with the polar surface to affect the viscoelastic, dielectric and/or refractive properties of the faceted structure, and thus affect the resonant cavity function that may shift, affect, or modulate the stimulated emission (peak 906).

Example 6

Target Species Differentiation

A schematic illustration of an array 920 is shown in FIG. 11. The array is produced in a manner similar to the array in Example 1, except that a plurality of electrical contacts 930 apply a voltage bias through the corresponding faceted structures 10 and across a conductive substrate 932 to a back metallization layer 934. An insulation layer 940, e.g. aluminum oxide, overlays and electrically insulates the electrical contacts.

During use, target species of differing polarities contact the exposed surfaces of the faceted structures in the array. A target species needs a sufficiently large polar moment to adhere to any of the exposed surfaces, as indicated by reference number 950. Because the exposed surfaces differ in surface area from faceted structure to faceted structure, there is an amount of surface area below which the target species will not adhere (a portion of non-adhering target species is indicated by reference number 952).

A reference faceted structure 960 is provided to which few or no target species will adhere due to the little or no exposed polar surface area. If a target species adheres to the exposed polar surface, then the faceted structure experiences a modulation in the depletion region that can be detected and measured. The detection and measurement can include at least one of current, voltage, or capacitance, from the electrical contacts to the back metallization layer. The change can be relative to what the property is in the absence of the target species, relative to the reference faceted structure, or both. As the polarity, or tendency to adhere to the polar surface, differs from target species to target species, differing target species are distinguishable from each other.

Reference is made to substances, components, or ingredients in existence at the time just before first contacted, formed in situ, blended, or mixed with one or more other substances, components, or ingredients in accordance with the present disclosure. As used herein, interaction refers to a chemical interaction that forms a non-covalently bound species modifying the electronic nature of the interacting intermediates. That is, an interaction refers to two or more chemical compositions in equilibrium. A substance, component or ingredient identified as a reaction product, resulting mixture, or the like may gain an identity, property, or character through a chemical reaction or transformation during the course of contact. That is, a reaction product may form a distinct chemical identity separate from the initial reactants, and that new identity may be based on, for example, covalent bonding. In the range of permanency between an electronic interaction and a chemical reaction, there exists a plurality of states: ionic bonding, complexing, and ligand formation, for example. For purposes of this disclosure, it is necessary to classify these intermediate states as reaction products unless context or language indicates otherwise. Hence, interaction includes electronic interactions such as the equilibrium adsorption of gas phase molecules onto a surface, and reaction includes a relatively more longer-lasting chemical relationship.

The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant, target species, or a solvent). Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

The embodiments described herein are examples of compositions, structures, systems, and methods having elements corresponding to the elements of the invention recited in the claims. This written description may enable those of ordinary skill in the art to make and use embodiments having alternative elements that likewise correspond to the elements of the invention recited in the claims. The scope of the invention thus includes compositions, structures, systems and methods that do not differ from the literal language of the claims, and further includes other structures, systems and methods with insubstantial differences from the literal language of the claims. While only certain features and embodiments have been illustrated and described herein, many modifications and changes may occur to one of ordinary skill in the relevant art. The appended claims cover all such modifications and changes.

The invention claimed is:

1. An apparatus, comprising:
a substrate;
an array of faceted structures disposed on a first surface of said substrate, wherein each faceted structure of said array comprises a sensor layer operable to react or to interact with at least one target species when the at least one target species is sufficiently proximate to said sensor layer, said sensor layer is capable of responding to the reaction or to the interaction in a detectable manner, and wherein each said faceted structure differs in at least one property across said array to define a gradient in said at least one property, wherein said array comprises a two-dimensional array and said at least one property comprises a first property and a second property, said first property of each said faceted structure is based on a first position of said faceted structure in said array along a first of the two dimensions, said second property of each said faceted structure is based on a second position of said faceted structure in said array along a second of the two dimensions, wherein said first property is a geometry of each said faceted structure and said second property is a composition of each said faceted structure; and
a detector operable to detect a response to the reaction, or to the interaction, of the target species with the sensor layer.

2. The apparatus as defined in claim 1, wherein said substrate is capable of resisting degradation in an environment of increased pressure, increased temperature, or reactive chemicals.

3. The apparatus as defined in claim 1, wherein said substrate is ceramic, or is a ceramic-coated metal, and has one or more electrical leads or circuits encased by the ceramic or ceramic coating.

4. The apparatus as defined in claim 1, wherein said substrate is a crystalline semiconductor material.

5. The apparatus as defined in claim 1, wherein said substrate is capable of transmitting radiation though said substrate and to said array of faceted structures, wherein the transmitted radiation can interact with each said faceted structure of said array to be changed, modulated, or changed and modulated in a detectable manner in the presence of the at least one target species reacted or interacted with said sensor layer, and said substrate is capable further of transmitting the changed, modulated, or changed and modulated transmitted radiation through said substrate.

6. The apparatus as defined in claim 1, wherein said detector is operable to detect a stimulated emission of radiation that has been changed, modulated, or changed and modulated by the reaction or interaction of the at least one target species with said sensor layer.

7. The apparatus as defined in claim 1, further comprising a radiation source capable of directing radiation to said array of faceted structures, wherein the radiation is of a quantity and of a type capable of eliciting a stimulated emission, a spontaneous emission, or both types of emission from said array of faceted structures.

8. The apparatus as defined in claim 1, wherein said detector is operable to generate a signal, and the apparatus further comprises a controller communicating with a radiation source and said detector, said controller being operable to initiate said radiation source to direct radiation to said array of faceted structures, and being operable further to receive the signal, wherein said array of faceted structures is capable of responding to the radiation by an emission, and said sensor layer is capable of modulating the emission in the presence of the at least one target species, and the signal differs based on whether the emission is modulated or is not modulated, and thereby said controller is capable of determining whether the at least one target species is present based on a difference in the signal.

9. The apparatus as defined in claim 1, wherein said apparatus includes a power source in communication with said detector, and a housing, and said apparatus is configured and housed to be of a weight and size sufficient to be a one-man portable unit.

10. The apparatus as defined in claim 1, wherein said apparatus is configured to be a stationary unit.

11. The apparatus as defined in claim 1, wherein at least one faceted structure of said array of faceted structures comprises metal-containing nitride.

12. The apparatus as defined in claim 11, wherein the at least one faceted structure comprises a surface, said faceted structure surface is a metal face.

13. The apparatus as defined in claim 1, wherein at least one faceted structure of said array of faceted structures is a hexagonal pyramid having a base with a maximum diameter that is less than about 100 micrometers.

14. The apparatus as defined in claim 13, wherein said at least one faceted structure is a hexagonal pyramid having a base with a maximum diameter that is less than about 100 nanometers.

15. The apparatus as defined in claim 13, wherein said at least one faceted structure is a truncated hexagonal pyramid having an exposed truncated surface that has a c-plane orientation, and said truncated hexagonal pyramid has sides that form corresponding angles with a base of said truncated hexagonal pyramid such that the angles are less than 90 degrees.

16. The apparatus as defined in claim 1, wherein at least one faceted structure of said array of faceted structures has a ratio of a polar surface area to a non-polar surface area that is in a range of from about 0.1 to about 0.75.

17. The apparatus as defined in claim 1, wherein said array of faceted structures comprises at least two faceted structures in a spatial relationship relative to each other.

18. The apparatus as defined in claim 1, wherein each said faceted structure in said array is spaced from a neighboring faceted structure in said array by a distance of less than about 10 micrometers.

19. The apparatus as defined in claim 1, wherein said substrate defines a first plane and said array is disposed in a second plane parallel to the first plane.

20. The apparatus as defined in claim 1, wherein said array is disposed to define an arcuate surface.

21. The apparatus as defined in claim 1, wherein at least one faceted structure of the array is sized and shaped to facilitate a Lotus Effect, thereby being operable to block water access to, and to provide vapor access to, at least a portion of a surface of said at least one faceted structure when said at least one faceted structure is contacted with a fluid and a vapor.

22. The apparatus as defined in claim 1, wherein said apparatus is configured to operate in vacuum.

23. The apparatus as defined in claim 1, wherein said apparatus is configured to operate at a temperature of 200 degrees Celsius or higher.

24. The apparatus as defined in claim 1, wherein said apparatus is configured to operate in gas.

25. The apparatus as defined in claim 1, wherein said apparatus is configured to operate in liquid.

26. The apparatus as defined in claim 1, wherein said sensor layer comprises pendant metallic and nitrogen atoms capable of interacting or of reacting with the target species.

27. The apparatus as defined in claim 1, wherein said sensor layer comprises one or more of a capture agent or a binder, and said capture agent or said binder is capable of interacting with, or reacting, with the target species.

28. The apparatus as defined in claim 27, wherein said capture agent or binder comprises one or more of an antibody, an antibody fragment, a protein, a peptide, an aptamer, and a biologically active small molecule.

29. The apparatus as defined in claim 1, wherein said sensor layer comprises a catalyst in an amount of greater than about 0.01 ppb.

30. The apparatus as defined in claim 29, wherein said catalyst is responsive to a gas species selected from the group consisting of NO, $NO_2$, $NH_3$, $CO_2$, CO, and $H_2$.

31. The apparatus as defined in claim 1, wherein said sensor layer has an average thickness of less than 100 micrometers.

32. The apparatus as defined in claim 1, wherein said sensor layer has an outward facing surface, and disposed on at least a portion of said outward facing surface is an exclusion layer.

33. The apparatus as defined in claim 32, wherein said exclusion layer is at least one of a size excluding layer, a selective chemical exclusion layer and a non-target species exclusion layer.

34. The apparatus as defined in claim 32, wherein said exclusion layer comprises at least one of a porous structure, a perforate structure, and a lipid bilayer.

35. The apparatus as defined in claim 1, wherein said sensor layer is one or more outermost monolayers disposed on a surface of each said faceted structure.

* * * * *